US012698246B2

(12) United States Patent
Wu et al.

(10) Patent No.: US 12,698,246 B2
(45) Date of Patent: *Aug. 4, 2026

(54) TRANSITION METAL CARBIDES FOR CATALYTIC DEHYDROGENATION OF SHORT ALKANES

(71) Applicants: IOWA STATE UNIVERSITY RESEARCH FOUNDATION, INC., Ames, IA (US); PURDUE RESEARCH FOUNDATION, West Lafayette, IN (US)

(72) Inventors: Yue Wu, Ames, IA (US); Zhe Li, Bothell, WA (US); Fan Yang, Ames, IA (US); Yang Xiao, Ruston, LA (US)

(73) Assignees: IOWA STATE UNIVERSITY RESEARCH FOUNDATION, INC., Ames, IA (US); PURDUE RESEARCH FOUNDATION, West Lafayette, IN (US)

( * ) Notice: Subject to any disclaimer, the term of this patent is extended or adjusted under 35 U.S.C. 154(b) by 353 days.

This patent is subject to a terminal disclaimer.

(21) Appl. No.: 18/487,469

(22) Filed: Oct. 16, 2023

(65) Prior Publication Data

US 2024/0140886 A1 May 2, 2024

Related U.S. Application Data

(60) Provisional application No. 63/379,815, filed on Oct. 17, 2022.

(51) Int. Cl.
*C07C 5/32* (2006.01)
*B01J 23/652* (2006.01)
(Continued)

(52) U.S. Cl.
CPC ........... *C07C 5/325* (2013.01); *B01J 23/6525* (2013.01); *B01J 27/22* (2013.01); *B01J 37/0201* (2013.01); *B01J 37/18* (2013.01); *C07C 2523/64* (2013.01)

(58) Field of Classification Search
CPC . C07C 5/325; C07C 2523/64; C07C 2521/04; C07C 2521/06; C07C 2521/18;
(Continued)

(56) References Cited

U.S. PATENT DOCUMENTS 10,967,363 B1 * 4/2021 Li ............................ B01J 27/24
11,524,279 B1 * 12/2022 Li ............................ C07C 2/76
(Continued)

FOREIGN PATENT DOCUMENTS

CA 2534819 C 7/2013

OTHER PUBLICATIONS

Aly et al., "Effect of Boron Promotion on Coke Formation during Propane Dehydrogenation over Pt/y-Al2O3 Catalysts", ACS Catal., 10, 5208-5216, Apr. 2020.
(Continued)

*Primary Examiner* — Prem C Singh
*Assistant Examiner* — Francis C Campanell
(74) *Attorney, Agent, or Firm* — Haukaas Fortius PLLC; Michael H. Haukaas; Raymond F. Horvath

(57) ABSTRACT

The disclosure provides a method of dehydrogenating hydrocarbons, such as $C_2$ or $C_3$ hydrocarbons, selectively and efficiently, to provide the corresponding alkylenes. The method is based on a Pt nanolayer catalyst over MXene (Pt/MXene) that shows resistance to coke deposition. The dehydrogenation conditions developed provided about 22% propane conversion and over 90% selectivity toward the desired propylene product, and the catalyst was stable for a 24-hour continuous run. The byproducts were ethane, eth-
(Continued)

ylene, and methane, and only trace amounts of coke deposition over the catalyst were detected. Similar dehydrogenation conditions provided about 18% ethane conversion and over 90% selectivity toward the desired ethylene product. A mass balance of greater than 96% was achieved in each case.

20 Claims, 21 Drawing Sheets

(51) Int. Cl.

| | | |
|---|---|---|
| *B01J 27/22* | (2006.01) | |
| *B01J 37/02* | (2006.01) | |
| *B01J 37/18* | (2006.01) | |

(58) Field of Classification Search
CPC ............ C07C 2523/28; C07C 2523/42; C07C 5/3337; B01J 23/6525; B01J 27/22; B01J 37/0201; B01J 37/18
USPC ......................................................... 585/660
See application file for complete search history.

(56) References Cited

U.S. PATENT DOCUMENTS

2019/0084904 A1    3/2019  Varma et al.
2020/0215517 A1*   7/2020  Miller ...................... B01J 37/08

OTHER PUBLICATIONS

De et al., "Stable Cr-MFI Catalysts for the Nonoxidative Dehydrogenation of Ethane: Catalytic Performance and Nature of the Active Sites", ACS Catal., 11, 3988-3995, Mar. 2021.

Hannagan et al., "First-principles design of a single-atom-alloy propane dehydrogenation catalyst", Science, 372, 1444-1447, Jun. 2021.

Hook et al., "Predicting Selectivity for Ethane Dehydrogenation and Coke Formation Pathways over Model Pt—M Surface Alloys with ab Initio and Scaling Methods", J. Phys. Chem., C 2017, 121, 17882-17892, Jul. 2017.

Li et al., "Direct methane activation by atomically thin platinum nanolayers on two-dimensional metal carbides", Nature Catalysis, 4, 882-891, Oct. 2021.

Li et al., "Reactive metal-support interactions at moderate temperature in two-dimensional niobium-carbide-supported platinum catalysts", Nature Catalysis, 1, 349-355, May 2018.

Li et al., "Two-dimensional atomically thin Pt layers on MXenes: The role of electronic effects during catalytic dehydrogenation of ethane and propane", Nano Res., 8pgs, Aug. 2023.

Li et al., "Two-dimensional transition metal carbides as supports for tuning the chemistry of catalytic nanoparticles", Nature Communications, 9, 5258, 8pgs, Dec. 2018.

Wang et al., "Coke Formation on Pt—Sn/Al2O3 Catalyst for Propane Dehydrogenation", Ind. Eng. Chem. Res., 57, 8647-8654, Jun. 2018.

Wang et al., "Modeling phase formation on catalyst surfaces: Coke formation and suppression in hydrocarbon environments", AlchE J., 67, 12, e17454, 35pgs, Sep. 2021.

* cited by examiner

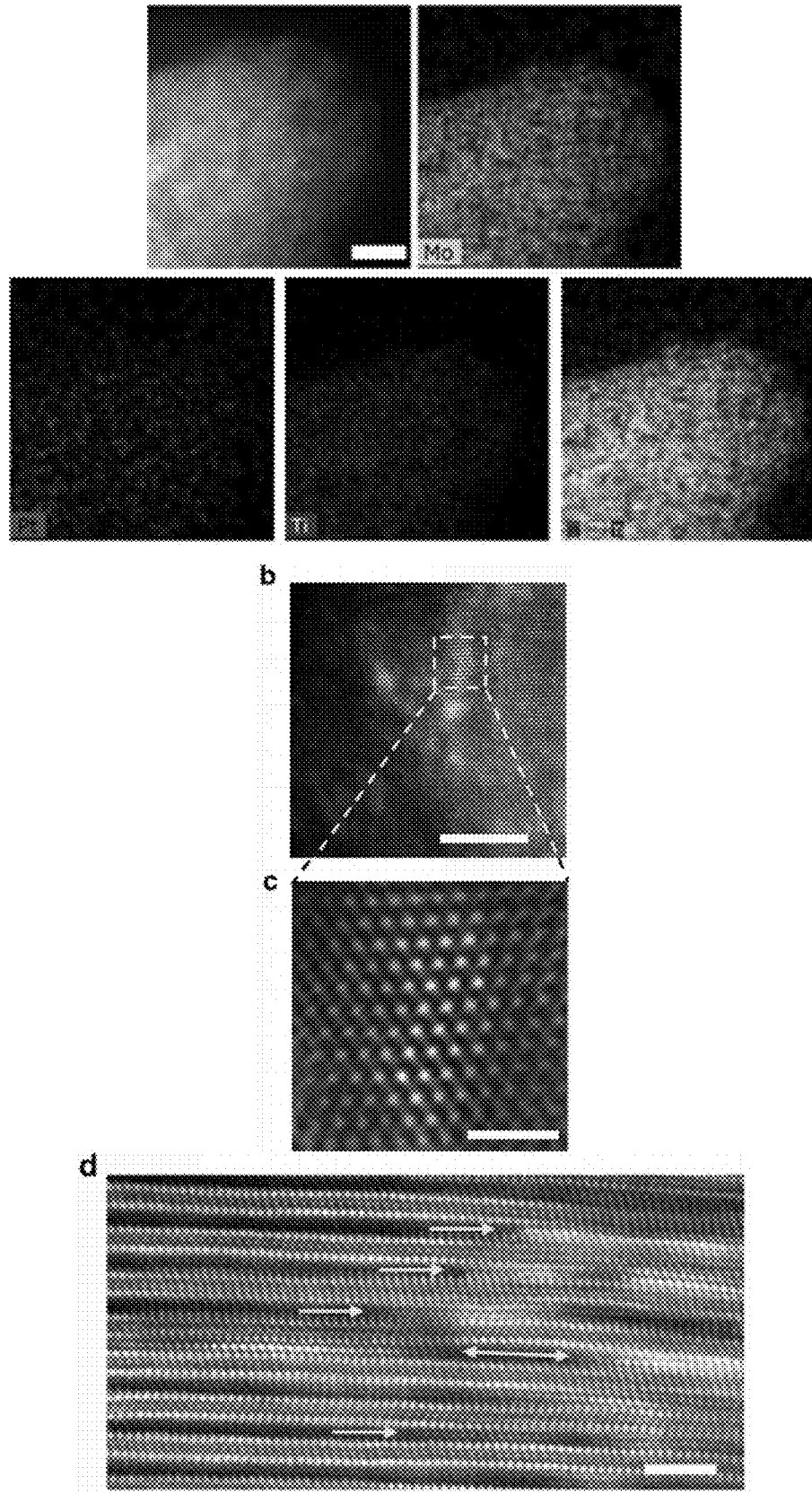
*Fig. 1A-D*

Ea ($C_2H_6$) = 164 kJ/mol

TRANSITION METAL CARBIDES FOR CATALYTIC DEHYDROGENATION OF SHORT ALKANES

RELATED APPLICATIONS

This application claims priority under 35 U.S.C. § 119(e) to U.S. Provisional Patent Application No. 63/379,815, filed Oct. 17, 2022, which is incorporated herein by reference.

BACKGROUND OF THE INVENTION

Ethylene ($C_2H_4$) and propylene ($C_3H_6$) are the first and second most important platform chemicals in the petrochemical industry. They have been traditionally produced via steam cracking of short-chain hydrocarbons (such as naphtha) and fluid catalytic cracking (FCC) of long-chain hydrocarbons (such as heavy gas oil), both of which consume a significant amount of energy and leave large carbon footprints. Due to its increasingly high-demand global market and motivation to utilize newly discovered shale gas resources, the production method has been shifting to the catalytic dehydrogenation of alkanes including ethane ($C_2H_6$) and propane ($C_3H_8$). Several commercial catalytic dehydrogenation processes have been developed, e.g., the Oleflex process by UOP, and the steam active reforming (STAR) process by Uhde (*Chem. Rev.* 2014, 114, 10613). Both previously mentioned processes employed supported Pt-based catalysts under operating temperatures and pressures at 525-705° C., 0.1-0.3 MPa, and 500-600° C., 0.6-0.9 MPa, respectively. Although Pt-based catalysts exhibit excellent activity for the catalytic dehydrogenation of ethane and propane, they suffer from rapid deactivation due to unavoidable coke formation onto the catalysts. The Oleflex process has to regenerate the deactivated catalysts every 5-10 days, while the STAR process shows severe catalyst deactivation within 7 h of time on stream (TOS).

Furthermore, the regeneration process is typically operated in an oxidative environment and at higher temperatures than 500-600° C., which may lead to the sintering of Pt nanoparticles, decreasing the lifetime of catalysts. Therefore, rapid deactivation and regeneration of catalysts are the major concerns for commercial catalytic dehydrogenation processes. To overcome these concerns, the development of coke-resistant catalysts and obtaining insights into the coke formation mechanisms are highly desired.

When the thickness of a supported metal is reduced to the atomic thin structure, the support has been found to play a substantial role in catalytic properties. It has been, however, challenging to understand the interaction between the support and the first metal layer and relate the effect of support to adsorptive and electronic properties that significantly impact the catalytic performance. The challenges lie in the difficulties in constructing metal species with atomic precision and selecting appropriate probe reactions that are sensitive to the adsorption capability of catalysts. The performance of alkane dehydrogenation catalysts, including the activity, selectivity, and stability, is known to be sensitive to the adsorptive and electronic properties of the active sites. For instance, Linic et al. reported that silica supported $Pt_1Sn_1$ nanoparticles delivered stable propylene selectivity at thermodynamically limited conversion levels (*Science* 2021, 373, 217). Similarly, Hook and Celik reported that the post-transition metal alloys exhibit lower binding energies of carbonaceous species and thus coke-resistant property was primarily due to the electronic effects rather than geometric effects (*J. Phys. Chem. C* 2017, 121, 17882).

These advances suggest that noble metal-based alloy nanoparticles can satisfactorily perform the dehydrogenation chemistry, but their working principles are still under debate. The main challenges are the coexistence of geometric (ensemble) and electronic effects on a checkerboard surface, leading to the complexity in evaluating the two coupled effects independently and the difficulty in relating the adsorptive and electronic properties of catalysts to their performance.

To overcome problems such as rapid catalyst deactivation and catalyst degradation during regeneration, further insights into the mechanism of coke formation will facilitate the highly desired development of a coke-resistant catalyst.

SUMMARY

Herein, we show that an atomically thin Pt nanolayer, with a single atomic layer thickness, supported on a two-dimensional molybdenum titanium carbide (MXene), decouples the electronic and geometric effects in selective dehydrogenation of ethane and propane. The nanolayer catalyst has large Pt ensembles that are similar to Pt nanoparticles. As compared with Pt nanoparticles, the Pt nanolayer structure exhibits different electronic properties, leading to superior performance for catalytic dehydrogenation of ethane and propane toward ethylene and propylene. In-situ spectroscopic and microscopic characterizations, combined with kinetic and theoretical studies, demonstrate that the improved catalytic performance results from weakened surface adsorption and tuned electronic structure of active sites.

Accordingly, this disclosure provides a method for dehydrogenating a hydrocarbon comprising:

a) activating a catalyst with a hydrogen source to provide an activated catalyst, wherein the catalyst comprises:

i) a MXene support of Formula I:

$$M_{n+1}X_nT_x \qquad (I);$$

wherein each M is independently an early transition metal; X is carbon or nitrogen; $T_x$ is a surface functional group wherein x is 0-10; and n is 1, 2, 3, or 4; and ii) a noble metal, wherein atoms of the noble metal occupy crystal lattice nodes at the basal plane of the MXene support, the atoms of the noble metal are supported by a metallic bond to the early transition metal, the noble metal has one to five nanostructured layers of its atoms on the MXene support, and loading of the noble metal on the MXene support is less than 5% w/w based on the weight of the catalyst; and b) contacting the activated catalyst and a hydrocarbon at a temperature of at least about 350° C., optionally in the presence of an inert gas, for a period of time sufficient to dehydrogenate the hydrocarbon;

thereby providing a non-oxidatively dehydrogenated hydrocarbon.

In some embodiments, the noble metal is platinum and the MXene support is $Mo_2TiC_2T_x$. In various embodiments, the hydrocarbon is propane or ethane. Carrying out the dehydrogenation method for a period of 24 hours results in minimal coke formation on the catalyst and minimal reduction in catalyst efficiency.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1A-G. Structural characterization of the 0.5% $Pt/Mo_2TiC_2T_x$ catalyst reduced at 550° C. (a) HAADF-STEM image viewing from the [0001] direction and EDS elemental mappings for Mo, Pt, Ti, and all three elements, respectively. Scale bar: 5 nm. HAADF-STEM image viewing from the [0001] direction, scale bars: (b) 5 nm and (c) 1 nm, respectively. (d) Atomic-resolution HAADF-STEM image showing metal-support interfaces, scale bar: 2 nm. (e) In-situ Pt L III edge XANES spectra of 0.5% $Pt/Mo_2TiC_2T_x$ reduced at 550° C. compared to Pt foil. (f) In-situ magnitude of the Fourier transform of the k2-weighted EXAFS spectra of 0.5% $Pt/Mo_2TiC_2T_x$ reduced at 550° C. compared to Pt foil. (g) The unique Pt nanolayer has a similar geometric surface to Pt nanoparticles, enabling the investigations of the electronic effect on the catalytic performance, where the geometric effect is negligible. It is found that the electronic effect plays a critical role in dehydrogenative product selectivity and catalyst stability.

DETAILED DESCRIPTION

Figure 1E:
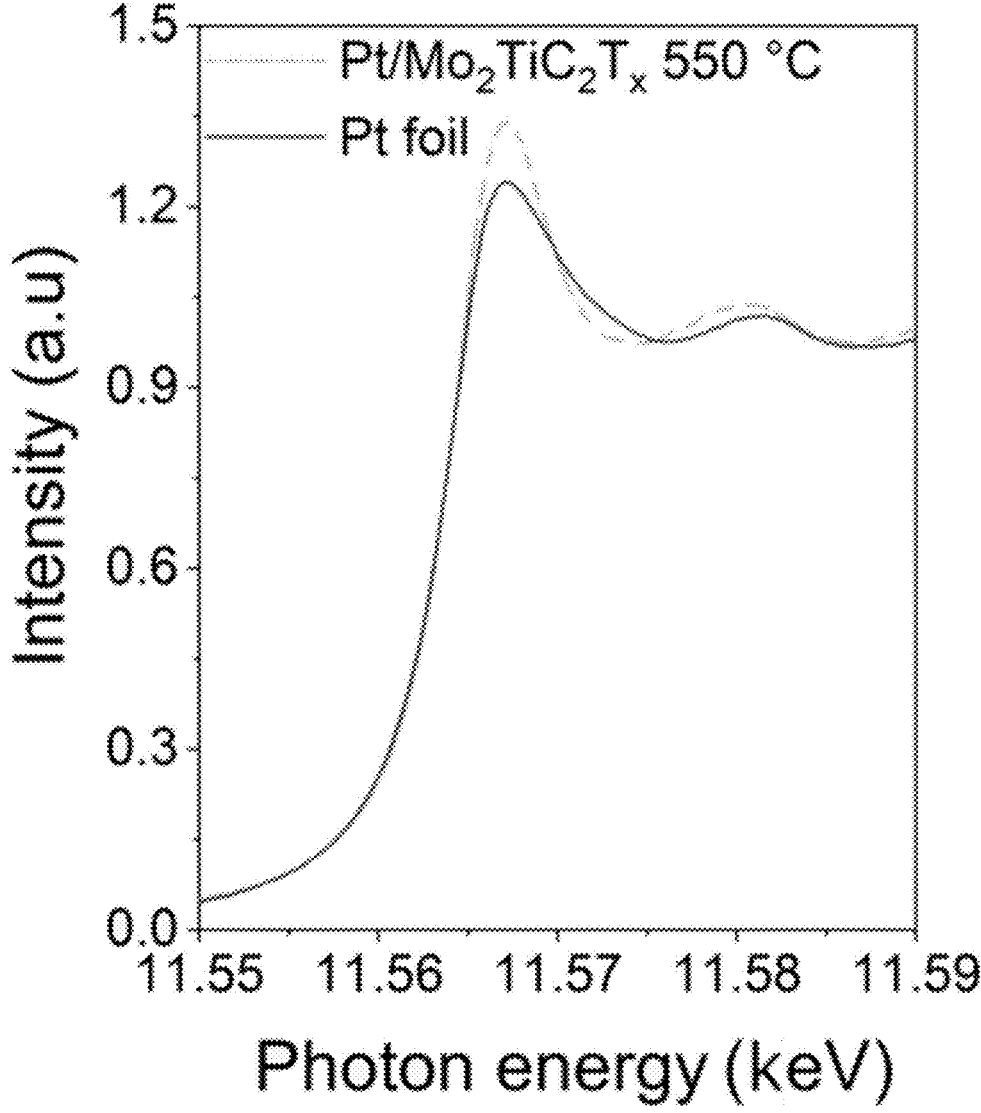

Atomically thin Pt nanolayers were synthesized on the surface of $Mo_2TiC_2$ MXenes and used for the catalytic dehydrogenation of ethane and propane into ethylene and propylene, two important chemicals for the petrochemical industry. As compared with Pt nanoparticles, the atomically thin Pt nanolayer catalyst showed superior coke-resistance (no deactivation for 24 h), high activity (turnover frequencies (TOFs) of 0.4-1.2 $s^{-1}$), and selectivity (>95%) toward ethylene and propylene. The unique Pt nanolayer has a similar geometric surface to Pt nanoparticles, enabling the investigations of the electronic effect on the catalytic performance, where the geometric effect is negligible. It is found that the electronic effect plays a critical role in dehydrogenative product selectivity and catalyst stability. The metal-support interaction is found to be dependent on the substrate and metal components, providing wide opportunities to explore high-performance MXene-supported metallic catalysts.

Additional information and data supporting the invention can be found in the following publication by the inventors: *Two-dimensional atomically thin Pt layers on MXenes: The role of electronic effects during catalytic dehydrogenation of ethane and propane, Nano Res.* (2023), doi.org/10.1007/s12274-023-6022-2 and its Supporting Information, which are incorporated herein by reference in their entirety.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability, necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

The recitation of a), b), c), . . . or i), ii), iii), or the like in a list of components or steps do not confer any particular order unless explicitly stated herein.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a chemical reaction or a physical change, e.g., in a solution or in a reaction mixture.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

The term "inert gas" refers to a substance that is not readily chemically reactive, such as nitrogen ($N_2$), carbon dioxide ($CO_2$), and the noble gases (helium, neon, argon, krypton, xenon, and radon).

The term "hydrocarbon", as used herein, refers to organic chemicals made up of only the elements carbon (C) and hydrogen (H). The hydrocarbon can be cyclic, linear unbranched or linear branched, and may be fully saturated or partially unsaturated. In some embodiments, the hydrocarbon is a $(C_2\text{-}C_8)$alkane, a $(C_2\text{-}C_6)$alkane, a $(C_2\text{-}C_4)$alkane, or a $(C_2\text{-}C_3)$alkane, and in particular, ethane or propane. In some embodiments, the hydrocarbon may be substituted with an atom of nitrogen, oxygen, or sulfur. In other embodiment, the framework of the hydrocarbon may be interrupted by an atom of nitrogen, oxygen, or sulfur.

As used herein, the terms "nonoxidative conditions" and "non-oxidative dehydrogenation" refer to the dehydrogenation process described herein wherein oxygen is not added to the reaction during dehydrogenation.

Embodiments of the Technology

This disclosure provides a method for dehydrogenating a hydrocarbon comprising:
- a) activating a catalyst with a hydrogen source to provide an activated catalyst, wherein the catalyst comprises:
  - i) a MXene support of Formula I:

$$M_{n+1}X_nT_x \qquad (I);$$

wherein each M is independently an early transition metal; X is carbon or nitrogen; $T_x$ is a surface functional group wherein x is 0-10; and n is 1, 2, 3, or 4; and
  - ii) a noble metal, wherein atoms of the noble metal occupy crystal lattice nodes at the basal plane of the MXene support, the atoms of the noble metal are supported by a metallic bond to the early transition metal, the noble metal has one to five nanostructured layers of its atoms on the MXene support, and loading of the noble metal on the MXene support is less than 5% w/w based on the weight of the catalyst; and
- b) contacting the activated catalyst and a hydrocarbon at a temperature of at least about 350° C., optionally in the presence of an inert gas, for a period of time sufficient to dehydrogenate the hydrocarbon;
  thereby providing a non-oxidatively dehydrogenated hydrocarbon.

In some embodiment, n is 2 or 3. In some embodiments, the noble metal is platinum, iridium, rhodium, palladium, ruthenium, or a combination thereof. In a preferred embodiment, the noble metal is platinum. In some embodiments, M is hafnium, niobium, molybdenum, titanium, tungsten, tantalum, chromium, vanadium, zirconium, or a combination thereof. In some embodiments, M is a combination of molybdenum and titanium. In some embodiments, the surface functional group $(T_x)$ is halo, hydroxyl, oxo, or a combination thereof. In some embodiments, the MXene support is $Mo_2TiC_2T_x$.

In some embodiments, the loading of the noble metal on the MXene support is about 0.1 weight percent to about 4.5 weight percent. In other embodiments, the loading is about 0.5 wt. %, about 1.0 wt. %, about 1.5 wt. %, about 2.0 wt. %, about 2.5 wt. %, about 3.0 wt. %, about 3.5 wt. %, about 4.0 wt. %, about 4.5 wt. %, or about 5.0 wt. %, with respect to the weight of the catalyst.

In some embodiments, the catalyst comprises about 0.1 wt. % to about 2 wt. % of the noble metal (for example, platinum) loaded on a $Mo_2TiC_2T_x$ support. In various embodiments, the wt. % of the noble metal loading is about 0.2, about 0.3, about 0.4, about 0.5, about 0.6, about 0.7, about 0.8, about 0.9, about 1.0, about 1.2, about 1.4, about 1.6, about 1.8, about 2.0, about 2.5, or about 3.0 wt/%.

In some embodiments, the activating comprises heating the catalyst and the hydrogen source at temperature above 250° C., wherein the hydrogen source is 30% v/v mixture of hydrogen gas in an inert gas. In other embodiments, the activating temperature is about 300° C., about 350° C., about 400° C., about 450° C., about 500° C., about 550° C., or about 600° C., or a range between any two of the aforementioned temperatures.

In some embodiments, the mixture comprises about 5% v/v to about 95% v/v of the hydrocarbon (e.g., ethane, propane, or another hydrocarbon recited herein). In other embodiments, the % v/v hydrocarbon in the mixture is about 10, about 20, about 30, about 40, about 50, about 60, about 70, or about 80% v/v. In some embodiments, the mixture comprises about 5% v/v to about 15% v/v of the hydrocarbon.

In some embodiments, the activated catalyst and the mixture are heated at a temperature of about 300° C. to about 800° C. In various embodiments, the heating temperature is about 200° C., about 250° C., about 300° C., about 350° C., about 400° C., about 450° C., about 500° C., about 550° C., about 600° C., about 650° C., about 700° C., about 750° C., or about 800° C., or a range between any two of the aforementioned temperatures. In certain specific embodiments, the activated catalyst and the mixture are heated at a temperature of about 500° C. to about 650° C.

In some embodiments, the hydrocarbon is propane or ethane. In various embodiments, the hydrocarbon can also be butane, pentane, hexane, heptane, octane, nonane, a $C_2$ to $C_{15}$ hydrocarbon, a $C_3$ to $C_{15}$ hydrocarbon, a $C_4$ to $C_{15}$ hydrocarbon, or a $C_5$ to $C_{15}$ hydrocarbon. In some embodiments, the hydrocarbon is dehydrogenated to provide propylene or ethylene, and in other embodiments, the hydrocarbon is dehydrogenated to provide butene, pentene, hexene, heptene, octene, nonene, a $C_2$ to $C_{15}$ mono-unsaturated hydrocarbon, a $C_3$ to $C_{15}$ mono-unsaturated hydrocarbon, a $C_4$ to $C_{15}$ mono-unsaturated hydrocarbon, a $C_5$ to $C_{15}$ mono-unsaturated hydrocarbon, or the corresponding $C_5$ to $C_{15}$ hydrocarbons with two, three, or four points of unsaturation.

In some embodiments, the contacting is at a gas hourly space velocity (GHSV) of about 100 cc/min to about 300 cc/min. In other embodiments, GHSV is about 50 cc/min, about 100 cc/min, about 150 cc/min, about 200 cc/min, about 250 cc/min, about 300 cc/min, about 350 cc/min, or about 400 cc/min. In some embodiments, an amount of the contacted activated catalyst (provided or used in the method) is about 100 mg to about 300 mg, typically about 50 cc/min to about 150 cc/min per 100 mg of catalyst. In various embodiments, the amount is about 100 mg, about 150 mg, about 200 mg, about 250 mg, about 300 mg, about 350 mg, about 400 mg, about 450 mg, or about 500 mg.

This disclosure also provides a method for dehydrogenating propane comprising:
- a) activating a catalyst by heating the catalyst in the presence of hydrogen gas to provide an activated catalyst, wherein the catalyst comprises:
  - i) a MXene support represented by Formula (II):

$$Mo_2TiC_2T_x \qquad (II);$$

wherein $T_x$ is a surface functional group wherein x is 0-10; and
  - ii) platinum metal, wherein atoms of the platinum metal occupy crystal lattice nodes at the basal plane of the MXene support, the atoms of the platinum metal are supported by a metallic bond to molybdenum atom of the MXene support, the platinum metal has one to five nanostructured layers of its atoms on the MXene support, and loading of the platinum metal on the MXene support is less than 5% w/w based on the weight of the catalyst; and b) contacting the activated catalyst and a mixture comprising propane and nitrogen gas at a temperature of at least about 350° C., for a period of time sufficient to dehydrogenate the propane;

thereby non-oxidatively dehydrogenating propane to provide propylene.

In some embodiments, the mixture comprising propane and nitrogen gas comprises about 5% v/v to about 25% v/v of propane, or about 5% v/v to about 15% v/v of propane. In some embodiments, the activated catalyst and the mixture are heated at a temperature of about 500° C. to about 600° C.

Additionally, this disclosure provides a method for dehydrogenating ethane comprising:

a) activating a catalyst by heating the catalyst in the presence of hydrogen gas to provide an activated catalyst, wherein the catalyst comprises:

i) a MXene support represented by Formula (II):

$$Mo_2TiC_2T_x \qquad (II);$$

wherein $T_x$ is a surface functional group wherein x is 0-10;

ii) platinum metal, wherein atoms of the platinum metal occupy crystal lattice nodes at the basal plane of the MXene support, the atoms of the platinum metal are supported by a metallic bond to molybdenum atom of the MXene support, the platinum metal has one to five nanostructured layers of its atoms on the MXene support, and loading of the platinum metal on the MXene support is less than 5% w/w based on the weight of the catalyst; and b) contacting the activated catalyst and a mixture comprising ethane and nitrogen gas at a temperature of at least about 350° C., for a period of time sufficient to dehydrogenate the ethane;

thereby non-oxidatively dehydrogenating ethane to provide ethylene.

In some embodiments, the mixture comprises about 5% v/v to about 15% v/v of ethane. In some embodiments, the activated catalyst and the mixture comprising ethane and nitrogen gas are heated at a temperature of about 550° C. to about 650° C.

In various embodiments, the gas hourly space velocity (GHSV) in step b) is about 50 cc/min to about 150 cc/min per 100 mg of catalyst.

The catalyst can maintain stability under the alkane dehydrogenation conditions for extended periods of time. For example, the catalyst experiences deactivation of less than 4%, less than 3%, less than 2%, or less than 1%, after 24 hours of time one stream. The amount of coke on the catalyst after 24 hours of time on stream is generally less than about 50 mg/g of catalyst, less than about 45 mg/g of catalyst, less than about 40 mg/g of catalyst, less than about 38 mg/g of catalyst, less than about 37 mg/g of catalyst, less than about 35 mg/g of catalyst, less than about 30 mg/g of catalyst, or less than about 25 mg/g of catalyst, and as low as only several mg/g (e.g., 5-15), for example, as determined by analysis of temperature-programmed oxidation (TPO) data. In one specific embodiment, the amount of coke on the catalyst after 24 hours of time on stream is about 35 mg/g of catalyst or less.

Results and Discussion

In catalysis science, metal-support interaction is typically discussed in two aspects: electronic effects due to electronic perturbations at the interface of metal/support, and geometric effects related to variations in metal nanoparticle shape or crystallographic structure. However, geometric and electronic effects are not completely independent phenomena. For example, the change in metal particle size results in the change of the electron bandwidth as well as the exposed surface, topology, and active sites where the reaction takes place. Therefore, it is known to the catalysis community that decoupling the electronic effect and geometric effects is challenging. Our unique Pt monolayer catalyst supported on the $Mo_2TiC_2$ MXene has essentially the same surface geometry as the Pt nanoparticle, which allows us to study the electronic effect solely when the geometric effect is minimal.

To investigate the monolayer Pt surface of the $Mo_2TiC_2$ catalyst with atomic resolution and to identify the active metal-support interface, aberration-corrected HAADF-STEM was employed. As shown in the energy dispersive X-ray spectroscopy (EDS) elemental mapping image of the catalyst (FIG. 1a), Pt wets the surface of $Mo_2TiC_2$ evenly without forming noticeable nanoparticles or segregation. HAADF-STEM image from the [0001] direction (FIGS. 1b and 1c) confirmed the observation that Pt atoms preferentially occupy the hexagonal-close-packed (hcp) positions on the Mo layer, as evidenced by the rhombic patterns of Pt atoms. Due to this special configuration, the surface structure of the smooth monolayer Pt is very similar to a Pt nanoparticle surface with a size larger than 2 nm. Thus, the geometric effect contribution of Pt nanoparticles is essentially negligible and the electronic effect in this should be the major contributor to the enhanced coke-resistant property.

A more detailed HAADF-STEM image viewed along the [1120] zone axis (FIG. 1d) confirmed the atomic ordering of $Mo_2TiC_2$, where a layer of Ti is sandwiched between two Mo layers. The brighter atoms with higher Z contrast corresponding to Pt atom revealed that Pt forms a monolayer intercalated between two layers of $Mo_2TiC_2$ MXene. This phenomenon differs from our previous observation of Pt deposited on other transition metal MXenes such as $Ti_3C_2T_x$ and $Nb_3C_2T_x$, where the MXenes alloy with Pt and form intermetallic nanoparticles. This major difference indicated that the formation of monolayer Pt on MXenes is not induced by the space confinement between MXene layers, but the unique interaction between Mo layer and Pt instead. At the interface between the Pt and Mo layer of $Mo_2TiC_2$ MXene, it can be seen that Pt atoms deposited on the hcp positions of the Mo layer, indicating a layer-by-layer epitaxial growth of Pt on the MXene surface. These results suggest that Pt and the MXene surfaces have strong interaction. According to Wulff's theorem, the growth of Pt is determined by the metal-support bonding instead of surface energy.

Figure 1F:
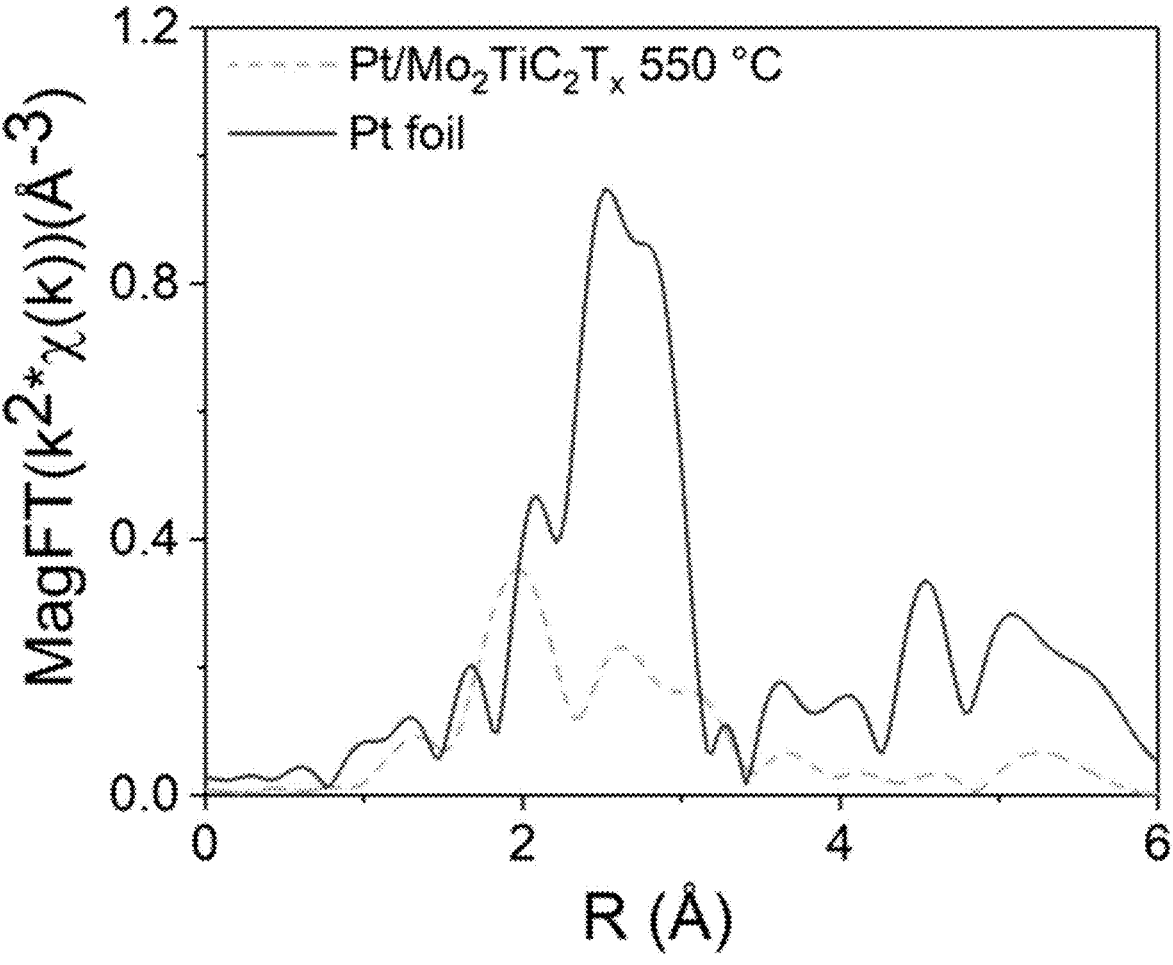

The chemical environment of the Pt nanolayer on $Mo_2TiC_2T_x$ and associated electronic effect were investigated using in-situ XAS. Comparing the $Pt/Mo_2TiC_2T_x$ catalysts reduced at 550° C. with metallic Pt foil, Pt LIII edge X-ray absorption near edge spectra (XANES) (FIG. 1e) show that the edge energy slightly increases from 11,564.0 to 11,564.8 eV while the whiteline intensity increases, which indicates more unoccupied Pt 5d states. The Fourier transform k2 weighted EXAFS spectra in FIG. 1f show that the scattering pattern of $Pt/Mo_2TiC_2T_x$ is very different from that of the Pt foil. The peak intensity is greatly reduced at R=2-3 Å (phase uncorrected distances), indicating strong deconstructive interference on Pt-5d (Pt—Pt) scattering by Pt-4d (Pt—Mo) scattering. Quantitative fitting of the EXAFS spectra gives the following average CNs and bond distances: 7.9 Pt—Pt bonds at 2.75 Å and 1.6 Pt—Mo bonds at 2.69 Å for the $Pt/Mo_2TiC_2T_x$ catalyst reduced at 550° C. (Table 1).

TABLE 1

Fitting results for the $k^2$ weighted EXAFS for $Pt/Mo_2TiC_2T_x$-R550° C.

| Sample | Scattering Pair | $S_0^2$* | CN | Bond Length (Å) # | $\sigma^2$ ($Å^2$) # | $\Delta E_0$ (eV) # |
|---|---|---|---|---|---|---|
| Pt Foil | Pt—Pt | 0.80 | 12 | 2.77 | 0.005 | 5.4 |
| $Pt/Mo_2TiC_2T_x$ | Pt—Pt | 0.80 | 7.9 | 2.75 | 0.014 | 4.0 |
| R550 C. | Pt—Mo | | 1.6 | 2.69 | 0.006 | |

*The $S_0^2$ for $Pt/Mo_2TiC_2T_x$ samples are fixed at the value (0.80) obtained by fitting the Pt Foil.
The average error in bond length is 0.01 Å, in $\sigma^2$ is 0.002 $Å^2$ and in $\Delta E_0$ is 0.9 eV.

The results indicate that the Pt nanolayers directly bond with the Mo atoms from the MXene support, which is consistent with HAADF-STEM showing that the Pt nanolayers are in direct contact with the Mo atom layers (FIGS. 1b and 1c), contributing to electronic effect of more unoccupied Pt 5d states in higher energy. All Pt/MXene catalysts in this work were activated/reduced at high temperatures in flow $H_2$, which were the same operating conditions as used in our prior work. Our prior work on quasi in-situ X-ray photoelectron spectroscopy (XPS) spectra has confirmed that the MXene surface functional groups were removed because both Mo—O peaks in the Mo 3d region and the F 1s peak disappeared as compared with the unreduced Pt/XMene catalysts (*Nat. Catal.* 2021, 4, 882).

Figure 2A:
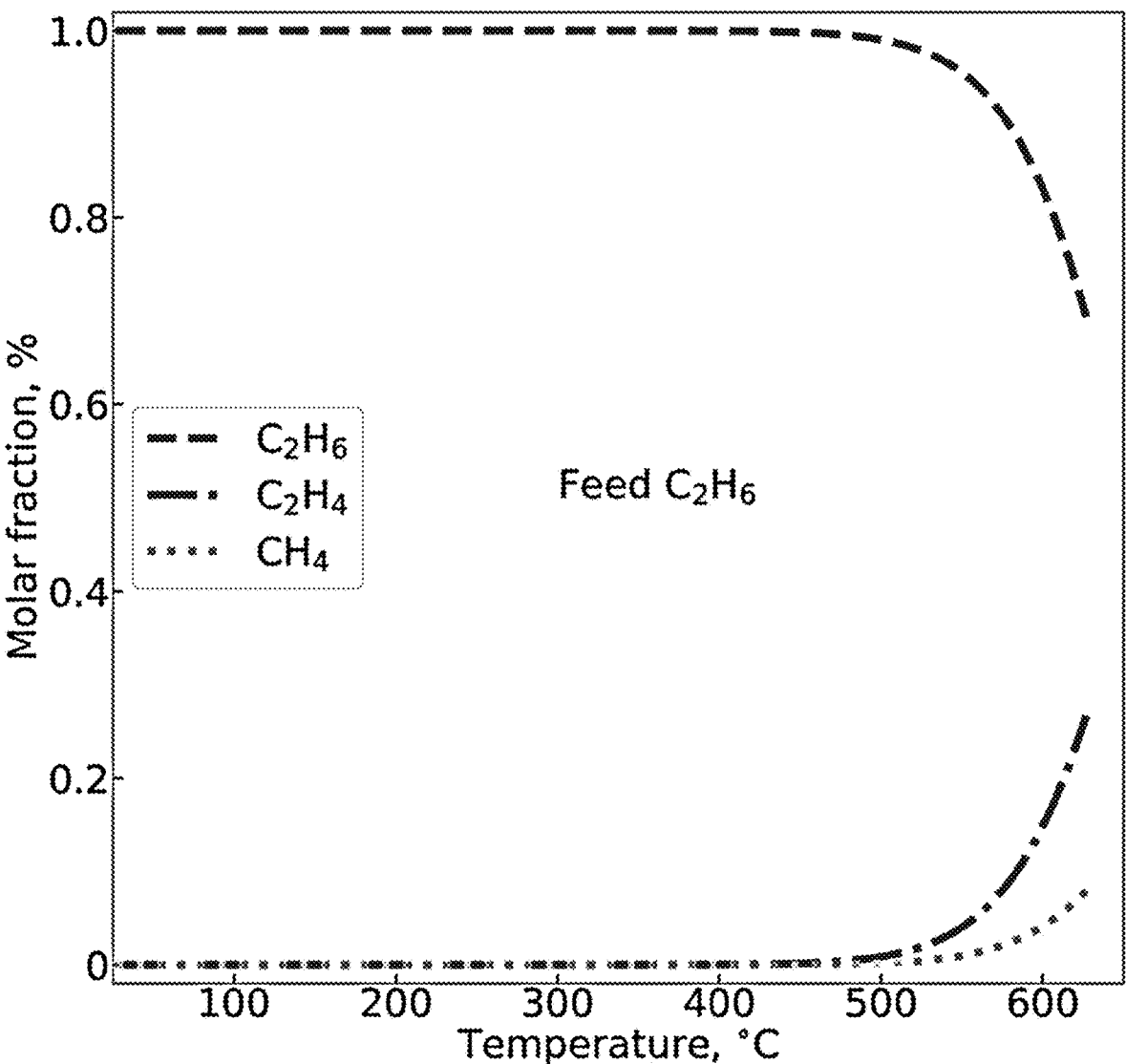
FIG. 2A-B. TPSR over 0.5% Pt/MXene for (a) ethane dehydrogenation at GHSV 57 $h^{-1}$ and (b) propane dehydrogenation at GHSV 119 $h^{-1}$.
Figure 2B:
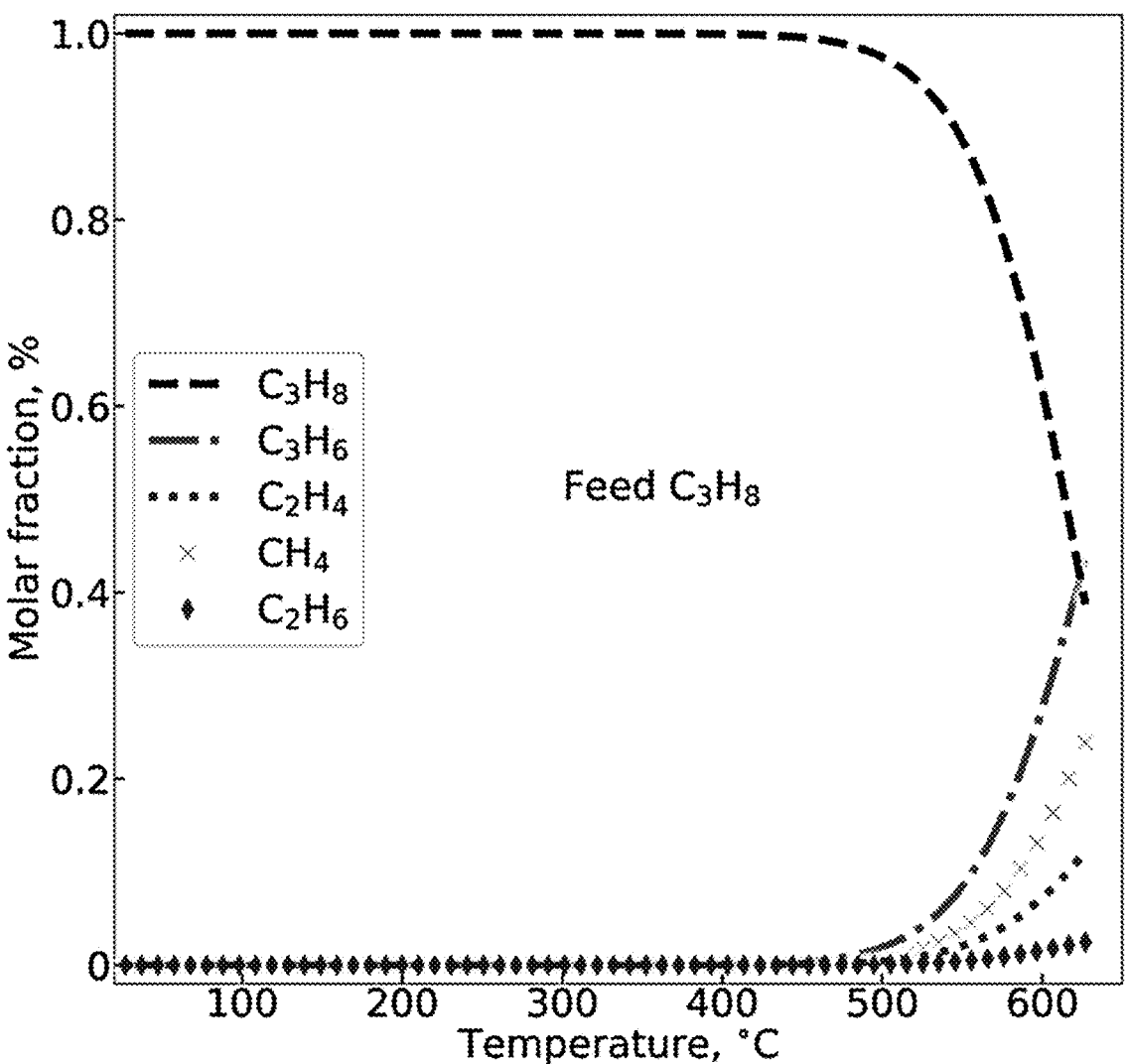
Figure 3A:
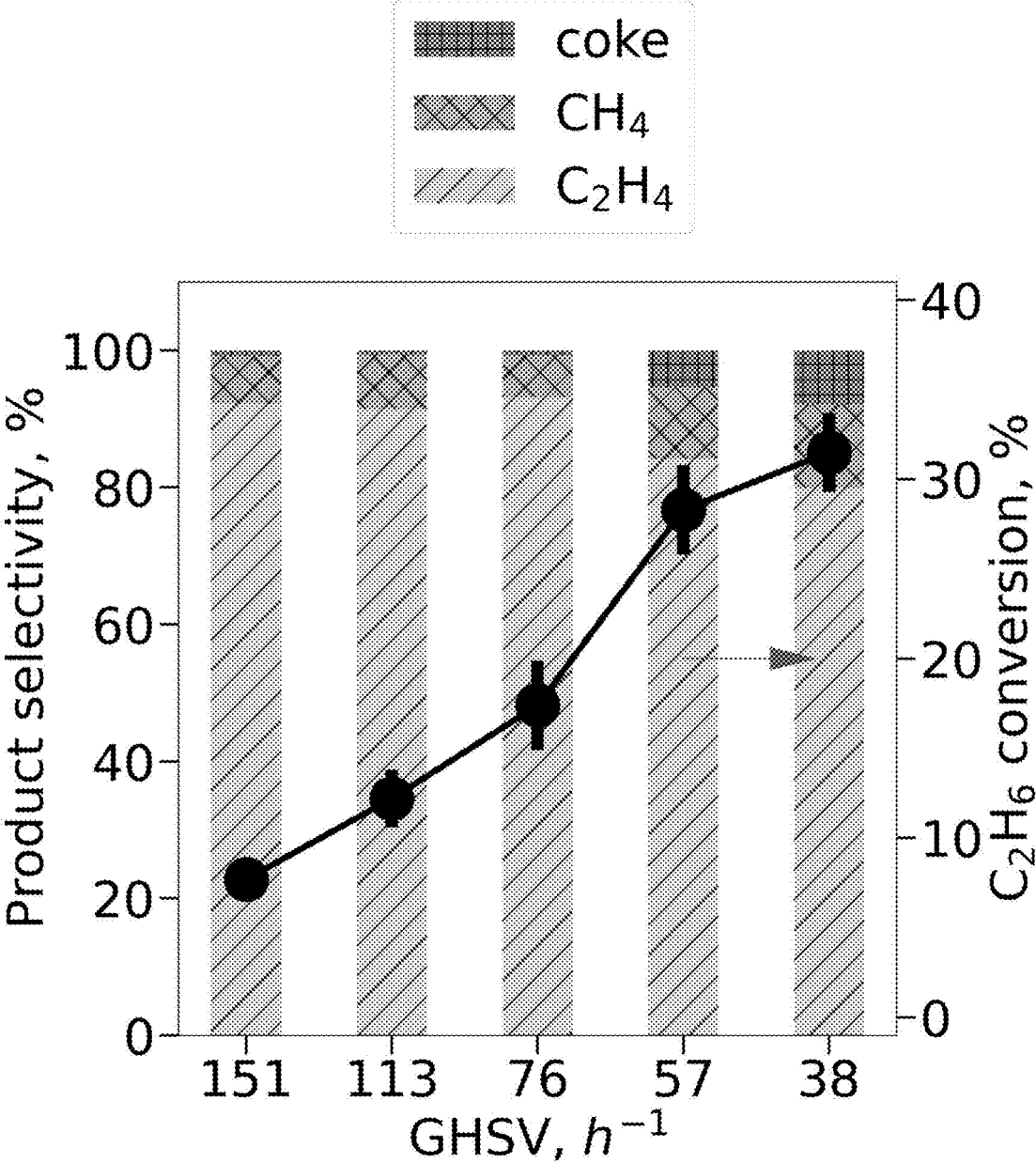
FIG. 3A-D. The catalytic performance of the 0.5% $Pt/Mo_2TiC_2$ catalyst for non-oxidative ethane and propane dehydrogenation. (a) Effect of GHSV on $C_2H_6$ dehydrogenation. (b) Effect of GHSV on $C_3H_8$ dehydrogenation. (c) Catalyst stability of $C_2H_6$ dehydrogenation. (d) Catalyst stability of $C_3H_8$ dehydrogenation. Operating conditions: at 550° C., 10% $C_2H_6$ or 10% $C_3H_8$ with balanced 89% $N_2$ and 1% Ar as an internal standard, 200 cc/min total flow rate, 200 or 100 mg catalyst for dehydrogenation of ethane or propane, respectively.
Figure 3B:
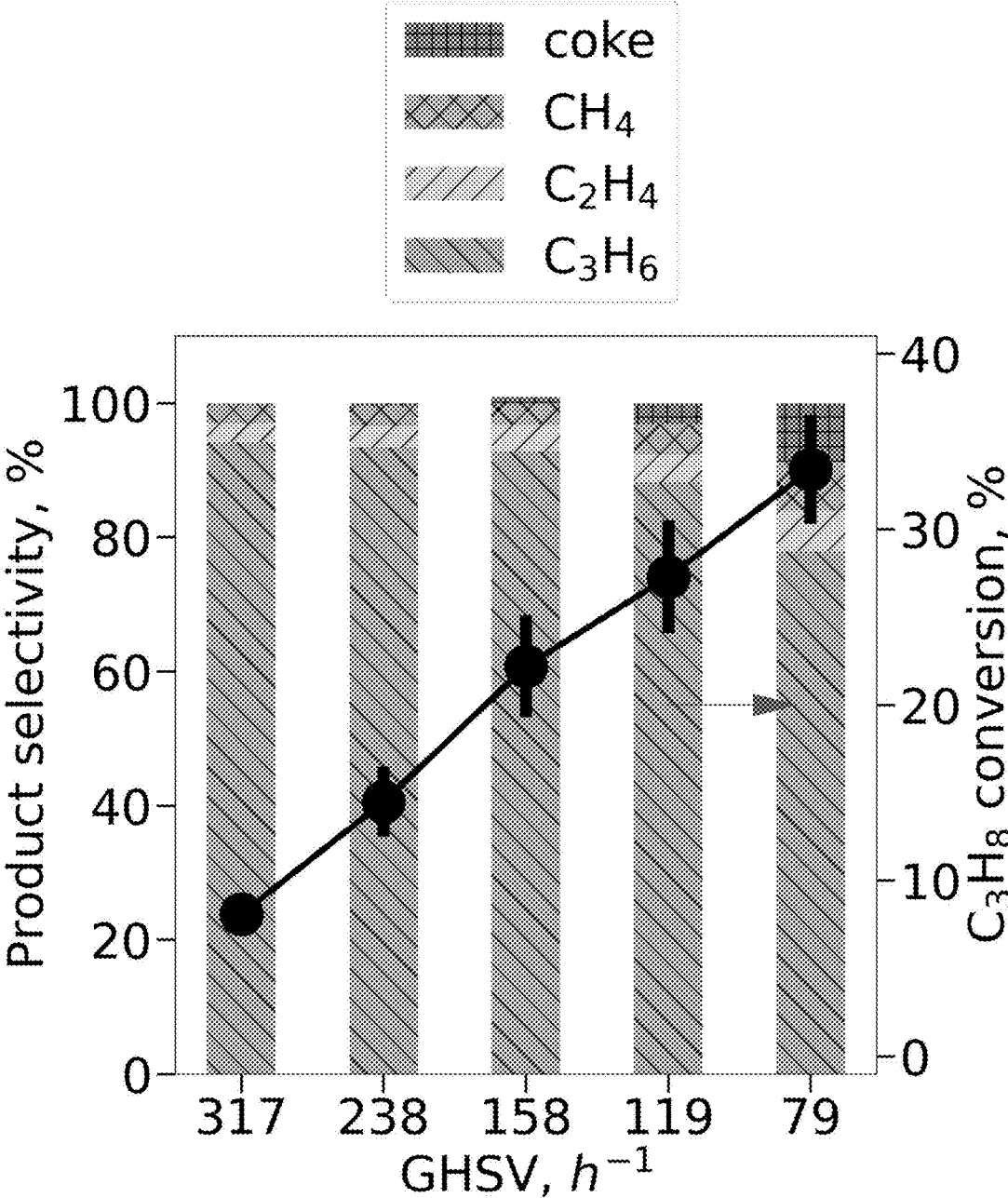

The activity of 0.5% $Pt/Mo_2TiC_2T_x$ for ethane and propane dehydrogenation was evaluated with a continuous-flow fixed-bed reactor. Low operating pressure and high temperature give higher equilibrium conversions of both ethane and propane dehydrogenation. Our investigations also found that relatively low operating pressure may prevent coke formation. Temperature-program surface reaction (TPSR) was used to determine the optimal reaction temperature for ethane and propane dehydrogenation (FIG. 2). The TPSR results show that ethane and propane cannot be activated over the $Pt/Mo_2TiC_2$ catalyst below about 500° C., while the selectivity towards desired olefin products, i.e., ethane to ethylene and propane to propylene, would drop as cracking reactions ($C_3H_8$ to $C_2H_4+CH_4$, $C_2H_6$ hydrogenolysis to $CH_4$). Therefore, in the catalytic performance tests, the reaction temperature was 550° C. and 0.1 MPa ethane or propane partial pressure. In FIGS. 3a and 3b, different GHSV values were achieved by varying the weight of packed catalysts and total flow rates. Mass balances of >95% were obtained for all reaction conditions.

As shown in FIG. 3a, the 0.5% $Pt/Mo_2TiC_2$ catalyst exhibited superior activity for catalytic ethane dehydrogenation with ethane conversion in the range of 8%-32% with high selectivity (80%-90%) towards ethylene. Note that when the GHSV was less than 57 $h^{-1}$, 5%-10% of coke was observed, indicating rapid deactivation. The main by-product of ethane dehydrogenation over the 0.5% $Pt/Mo_2TiC_2$ catalyst was methane ($CH_4$), which was formed by hydrogenolysis with in situ hydrogen from ethane dehydrogenation, i.e., $C_2H_6+H_2=2CH_4$. Similarly, catalytic dehydrogenation of propane showed the same trend of propane conversion vs. GHSV (FIG. 3b). Coke was observed at a higher starting GHSV (119 $h^{-1}$), while the selectivity towards propylene was typically in the range of 78%-95%.

Figure 3C:
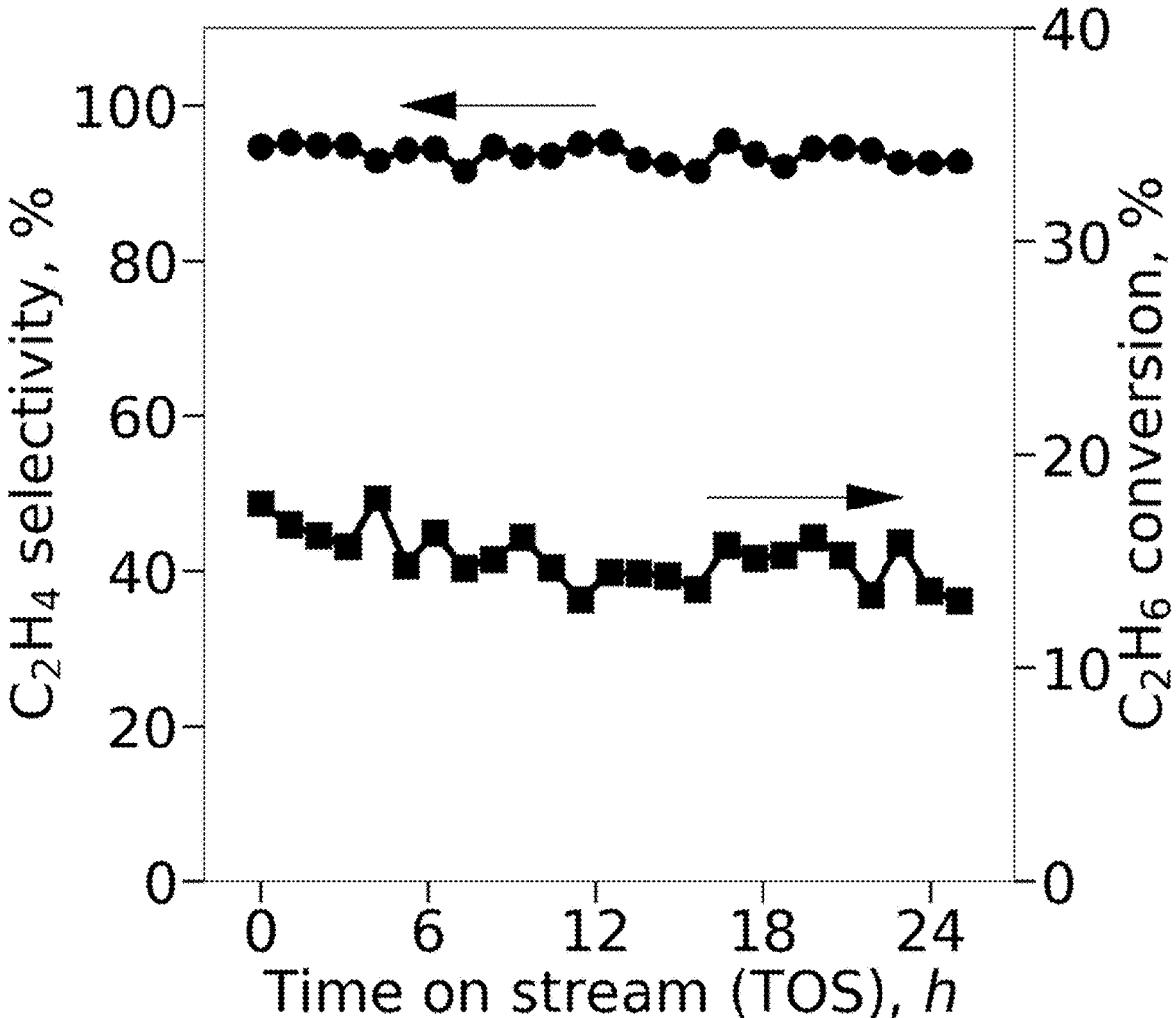
Figure 3D:
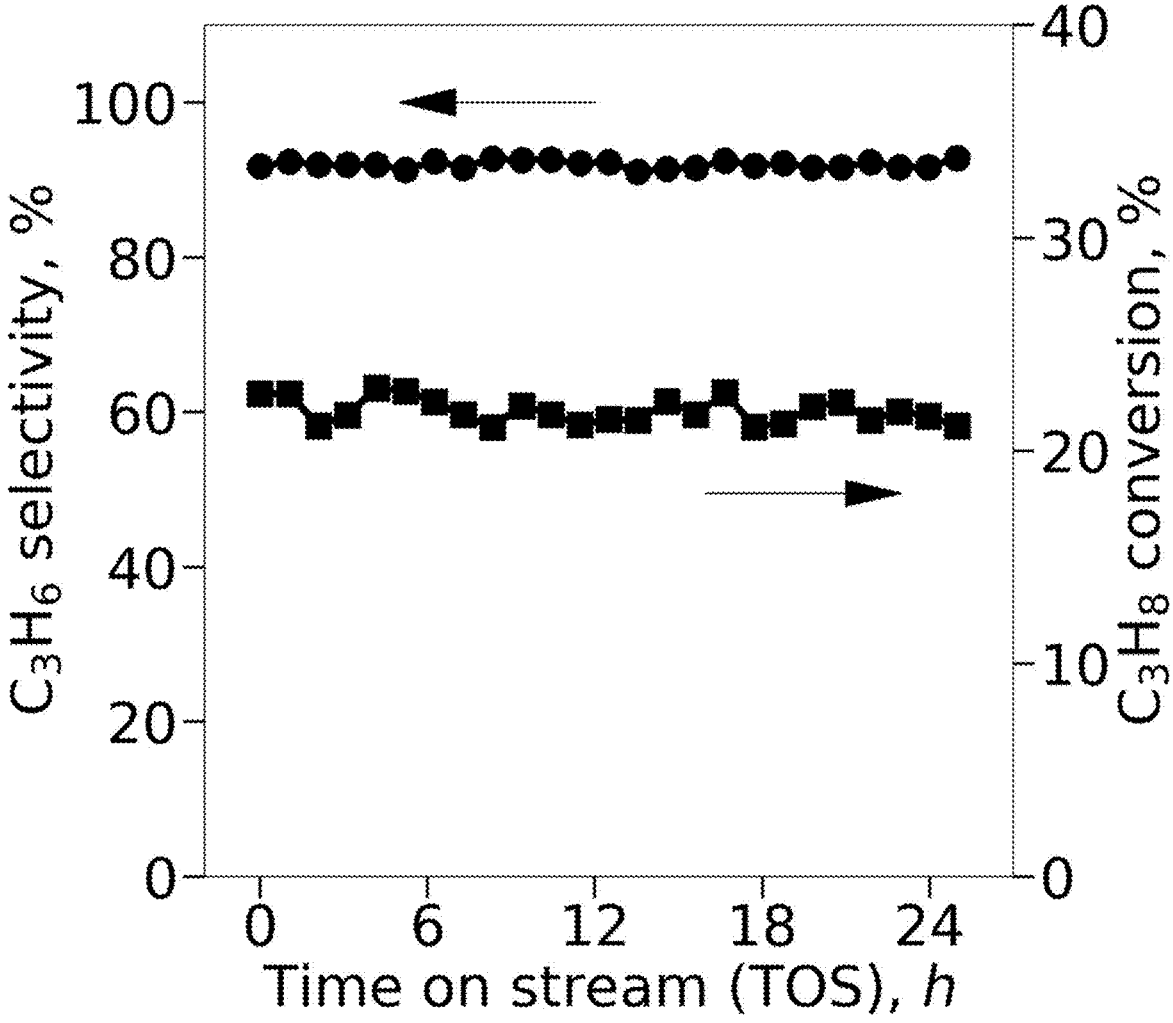
Figure 4A:
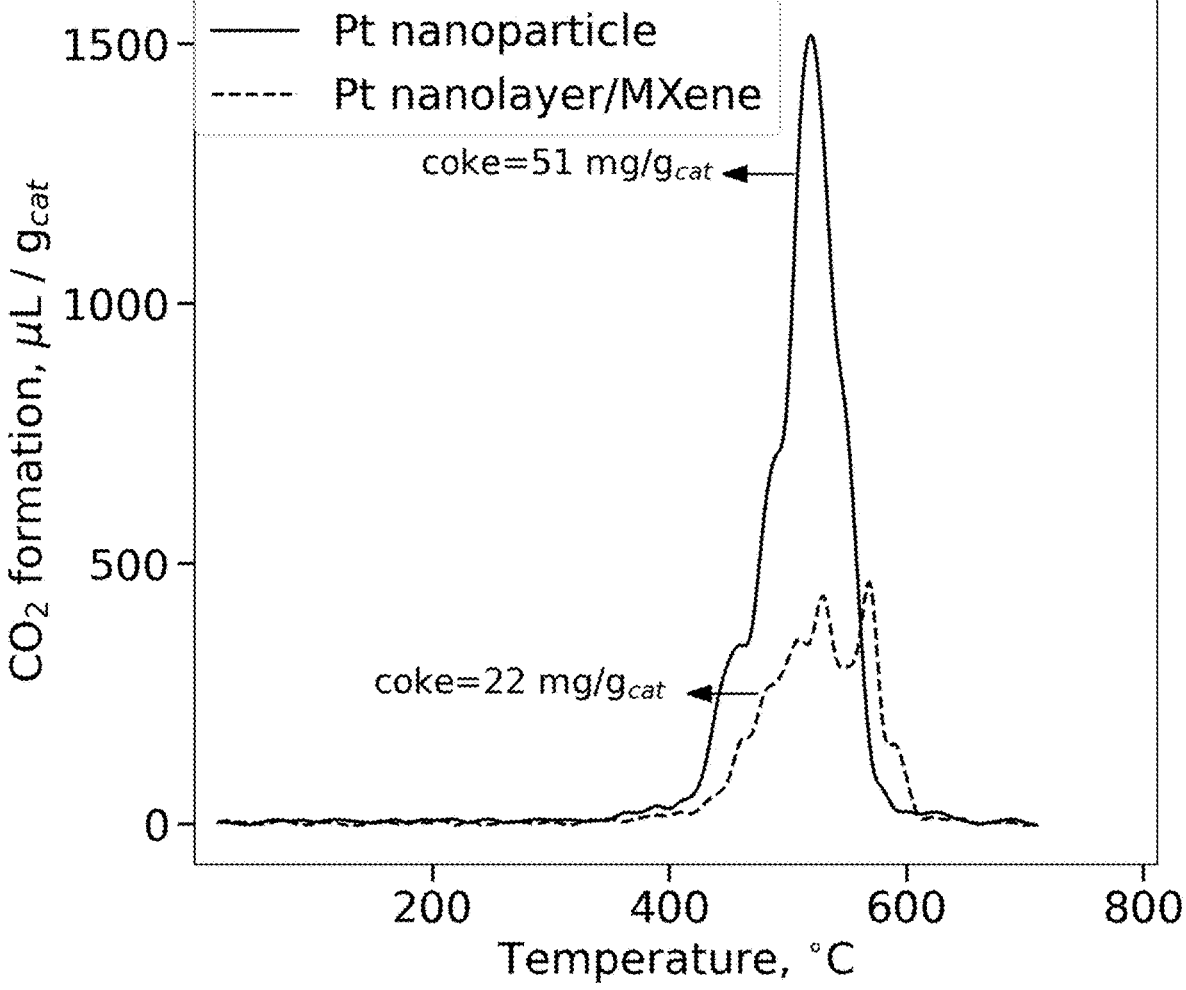
FIG. 4A-B. TPO profiles for 24-h spent 0.5% $Pt/Mo_2TiC_2T_x$ (Pt nanolayer/MXene, shallow curve) and 2-h spent 0.5% $Pt/SiO_2$ catalysts at 550° C. for (a) ethane dehydrogenation at GHSV 57 $h^{-1}$ and (b) propane dehydrogenation at GHSV 119 $h^{-1}$.
Figure 4B:
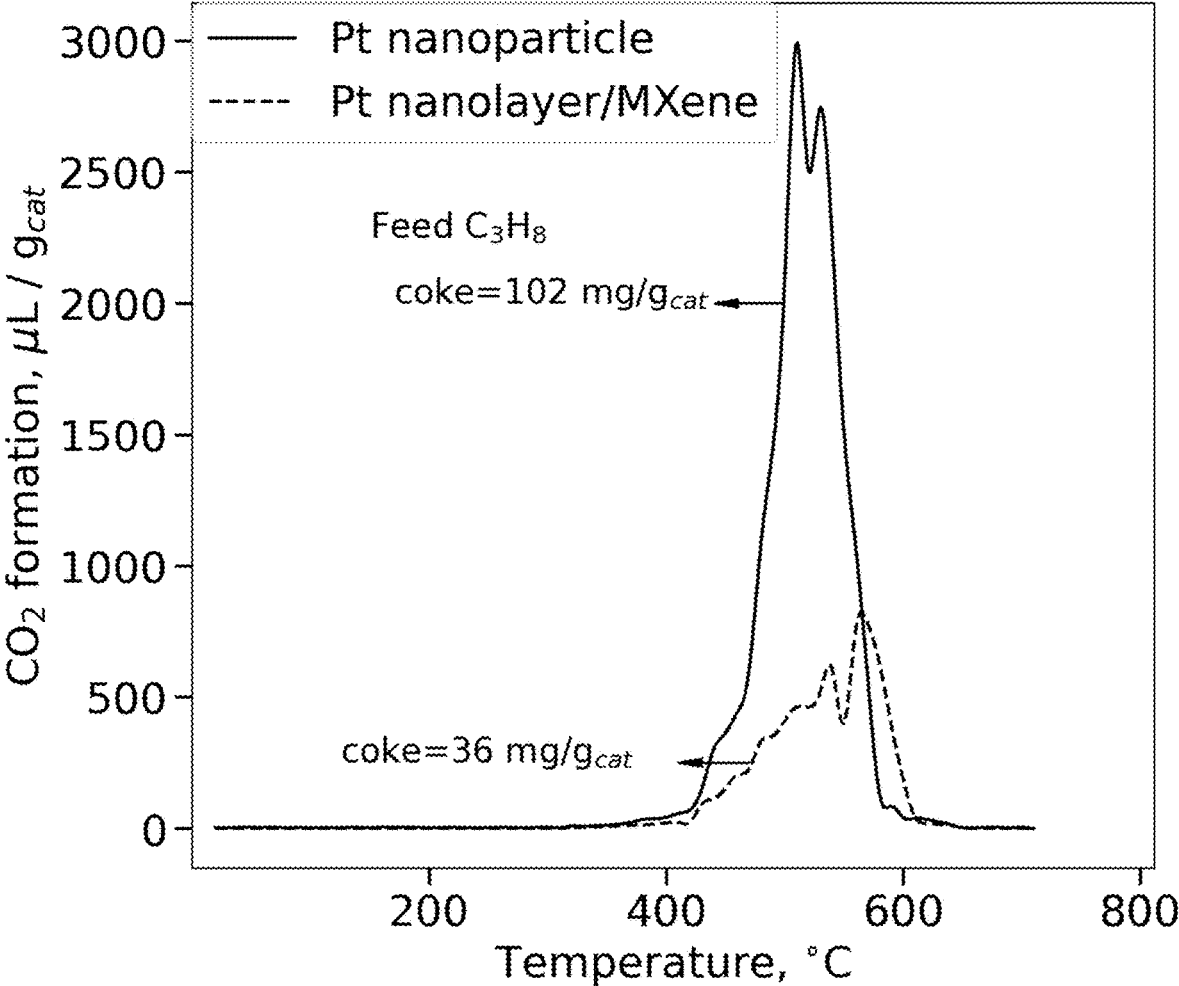
Figure 5A:
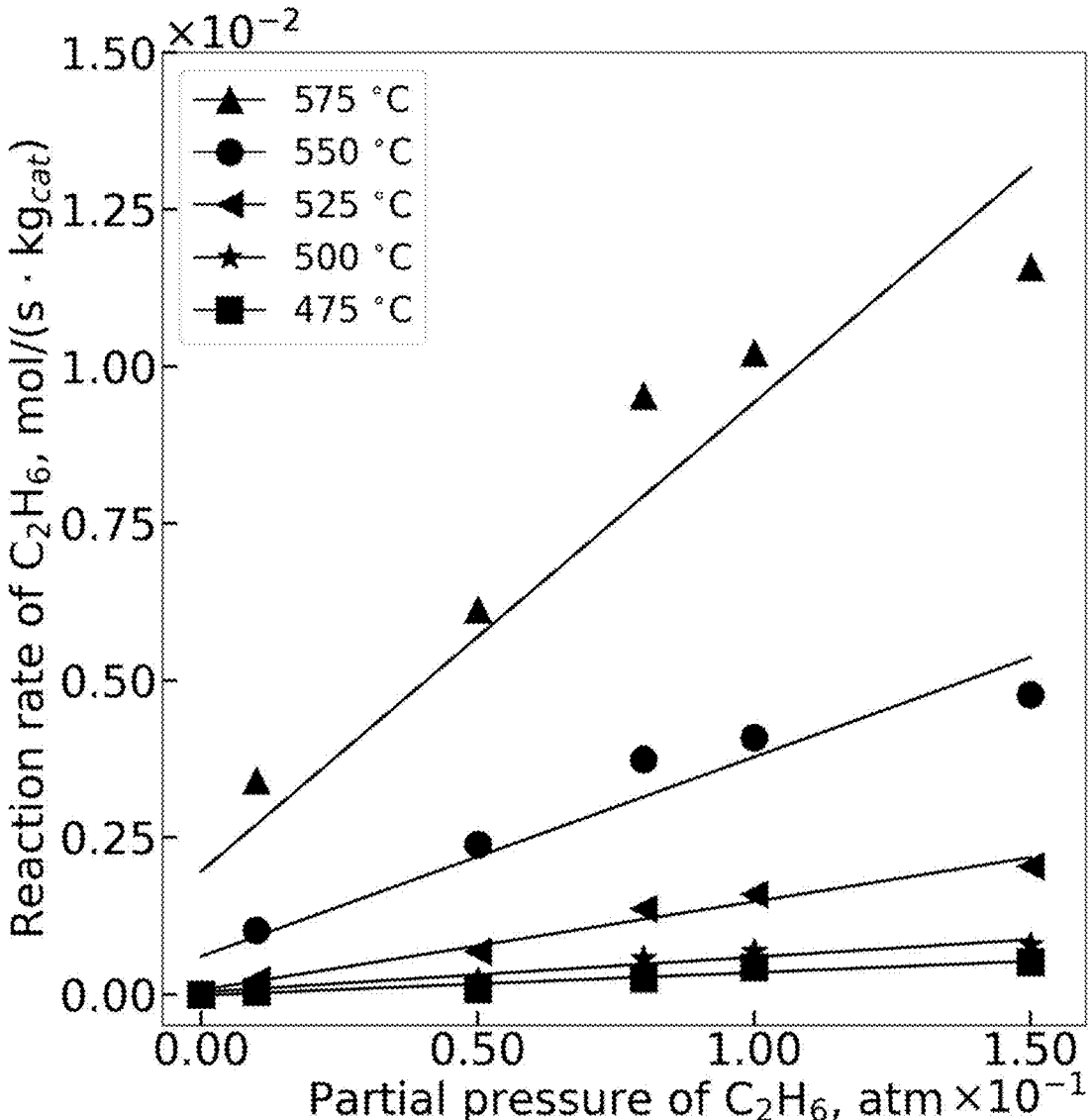
FIG. 5A-D. Investigations on ethane and propane kinetics, (a): fitting of ethane dehydrogenation, (b): Arrhenius plot for the rate constants of ethane dehydrogenation, (c): fitting of propane dehydrogenation, and (d): Arrhenius plot for the rate constants of propane dehydrogenation.
Figure 5B:
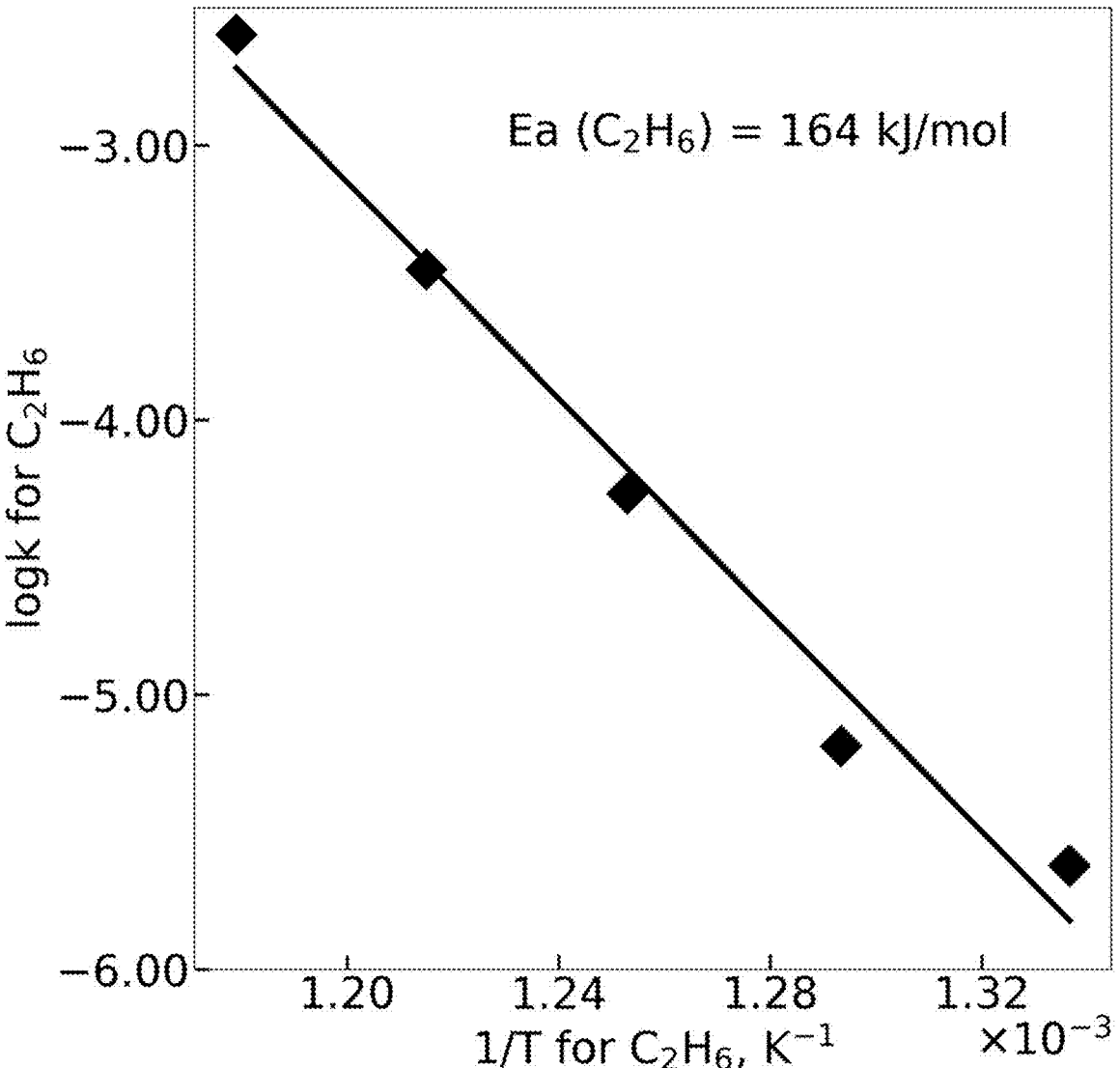
Figure 5C:
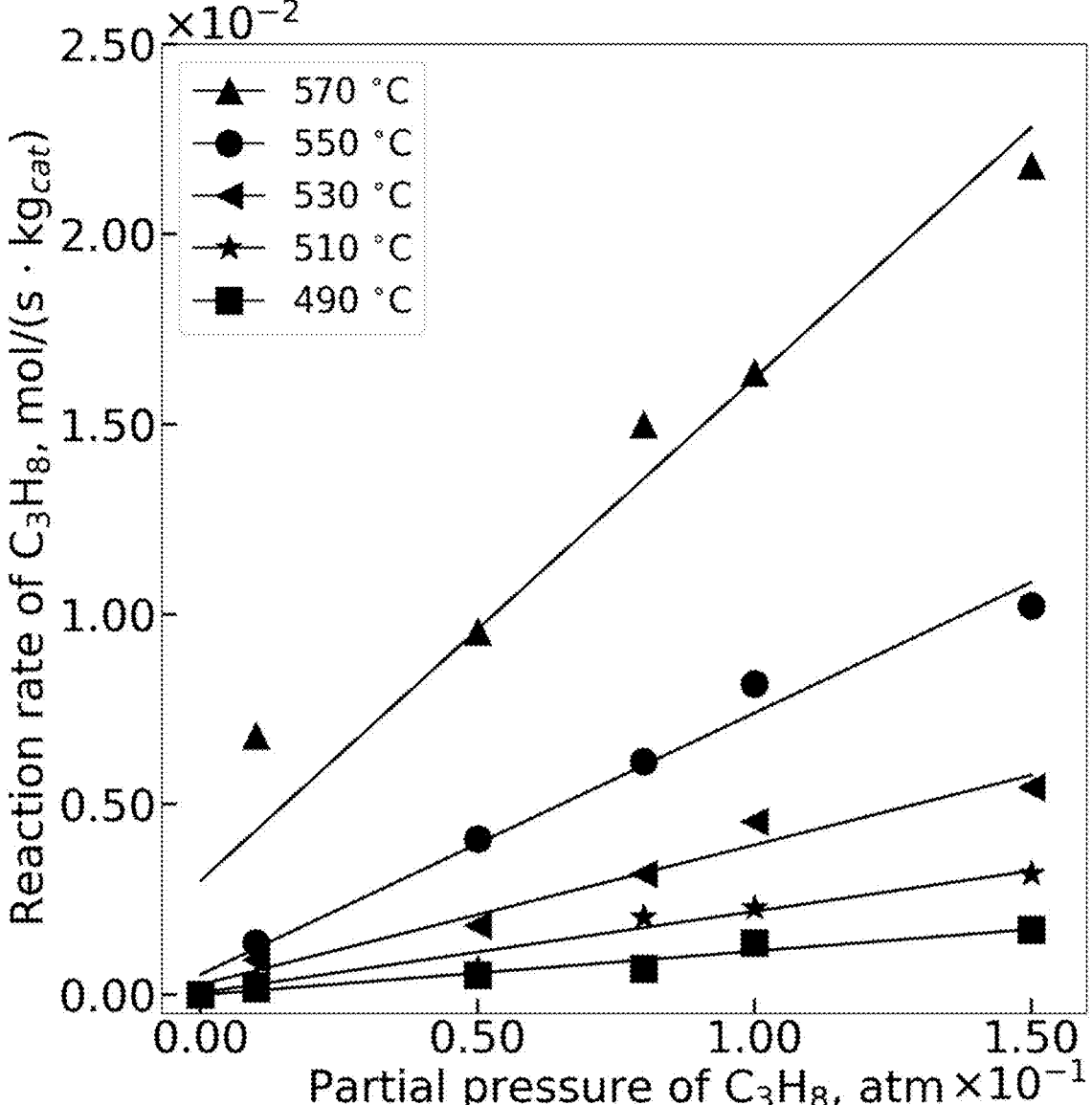
Figure 5D:
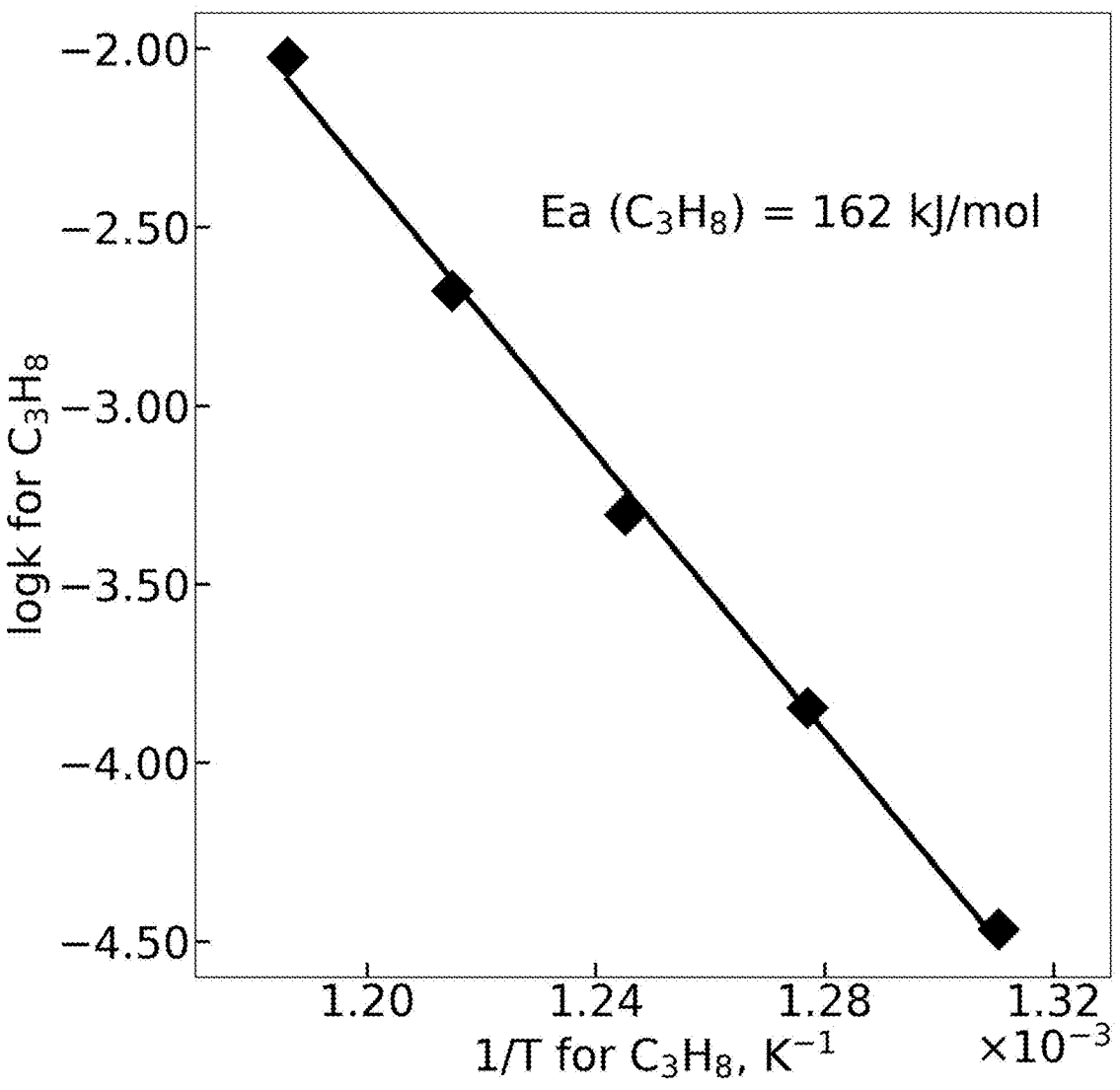

Remarkably, both reactions showed long-term stability, i.e., no observable deactivation with 24 h TOS with more than 95% selectivity at ~15% ethane conversion (FIGS. 3c) and 22% propane conversion (FIG. 3d), respectively. Temperature-programmed oxidation (TPO) of the 24 h spent Pt/MXene and 2 h spent $Pt/SiO_2$ catalysts (FIG. 4) shows that there is much less coke accumulation over Pt/MXene (22 $mg/g_{cat}$ for $C_2H_6$ dehydrogenation, and 36 $mg/g_{cat}$ for $C_3H_8$ dehydrogenation) than $Pt/SiO_2$ (51 $mg/g_{cat}$ for $C_2H_6$ dehydrogenation, and 102 $mg/g_{cat}$ for $C_3H_8$ dehydrogenation). It was found in our prior study that the XANES energy of the fresh $Pt/SiO_2$ catalyst was 11,564.0 eV. The fresh $Pt/SiO_2$ catalyst has an average Pt particle size of ~2-3 nm as measured by transmission electron microscopy (TEM) scans. The XRD patterns exhibited small peaks of the (111) and (200) planes at 39.2° and 45.6°, respectively, which is due to the relatively small Pt particle size (~2 nm). For the spent $Pt/SiO_2$ catalyst, however, both (111) and (200) peaks were stronger, which was likely due to the aggregation of Pt particles as measured by TEM. Both the fresh and spent Pt/MXene catalysts exhibited various peaks in XRD patterns, including (002) at 9.1°, (004) at 18.3°, (006) at 26.4°, (011) at 34.2°, (012) at 36.4°, (013) at 37.2°, (014) at 39.4°, (015) at 41.5°, (017) at 48.5°, and (010) at 59.1°, indicating excellent stability of Pt/MXene catalysts.

Figure 1G:
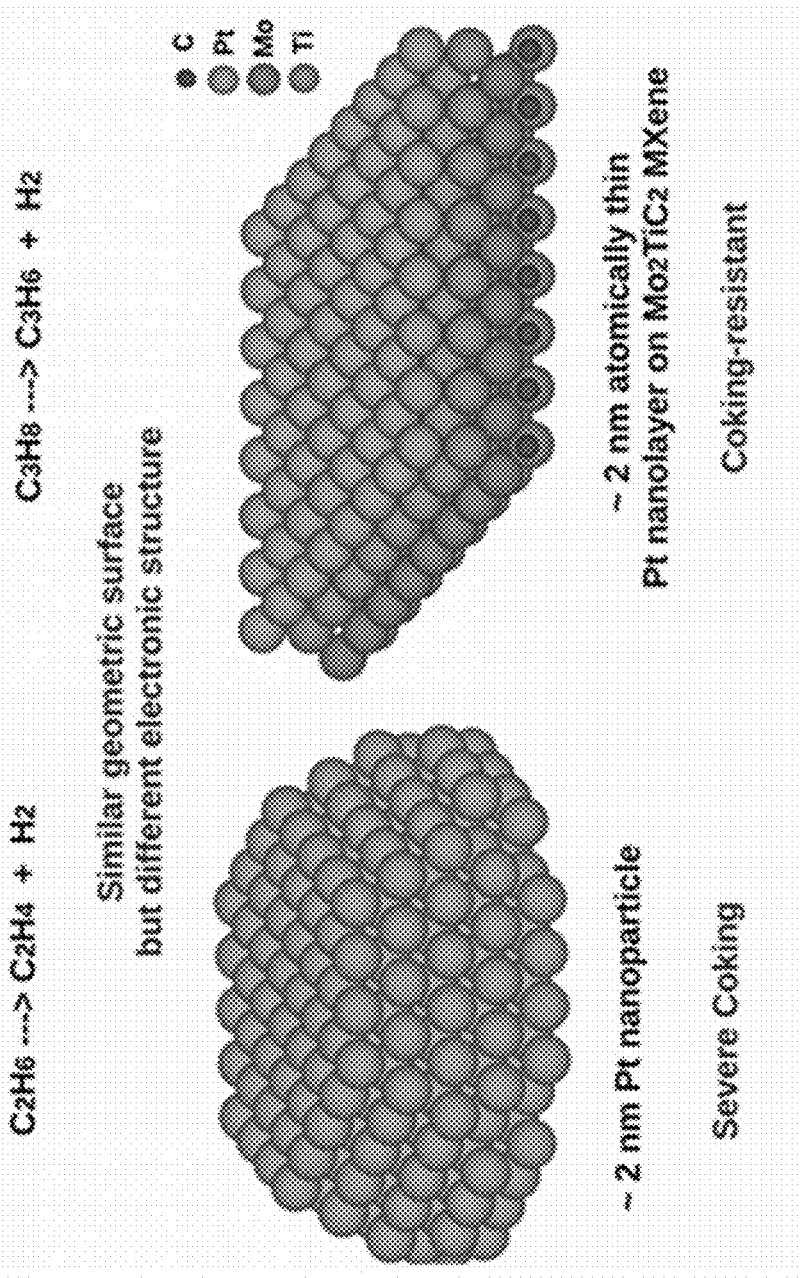

Both mass and heat transfer limitations were excluded prior to the measurement of reaction kinetics of ethane and propane dehydrogenation. A broader temperature range was investigated for the measurement of intrinsic kinetics in a differential reactor (conversion <15%) at 475-575° C. for ethane and 490-570° C. for propane. Both ethane and propane dehydrogenation reactions are the 1st order (FIG. 5), with activation energies of 164 and 162 $kJ \cdot mol^{-1}$, respectively, which is consistent with known values. These reaction rates were normalized by exposed surface Pt atoms, which were determined by Pt dispersion via the $H_2$—$O_2$ titration method, leading to turnover frequencies (TOFs). Pt dispersion refers to the ratio of surface Pt atoms to total Pt atoms. The Pt dispersion was >98%, indicating an atomically dispersed nanolayer structure shown in FIG. 1. Note that Pt dispersion was also measured by $H_2$ chemisorption and CO chemisorption (Table 2).

TABLE 2

Comparison of Pt dispersion measurements by $H_2$—$O_2$ titration, $H_2$ chemisorption and CO chemisorption.

| | $H_2$—$O_2$ titration | $H_2$ chemisorption | CO chemisorption |
|---|---|---|---|
| fresh $Pt/SiO_2$ | 31% | 33% | 35% |
| spent $Pt/SiO_2$ | 18% | 16% | 21% |
| fresh Pt/MXene | 98% | 95% | 93% |
| spent Pt/MXene | 98% | 94% | 94% |

Figure 6A:
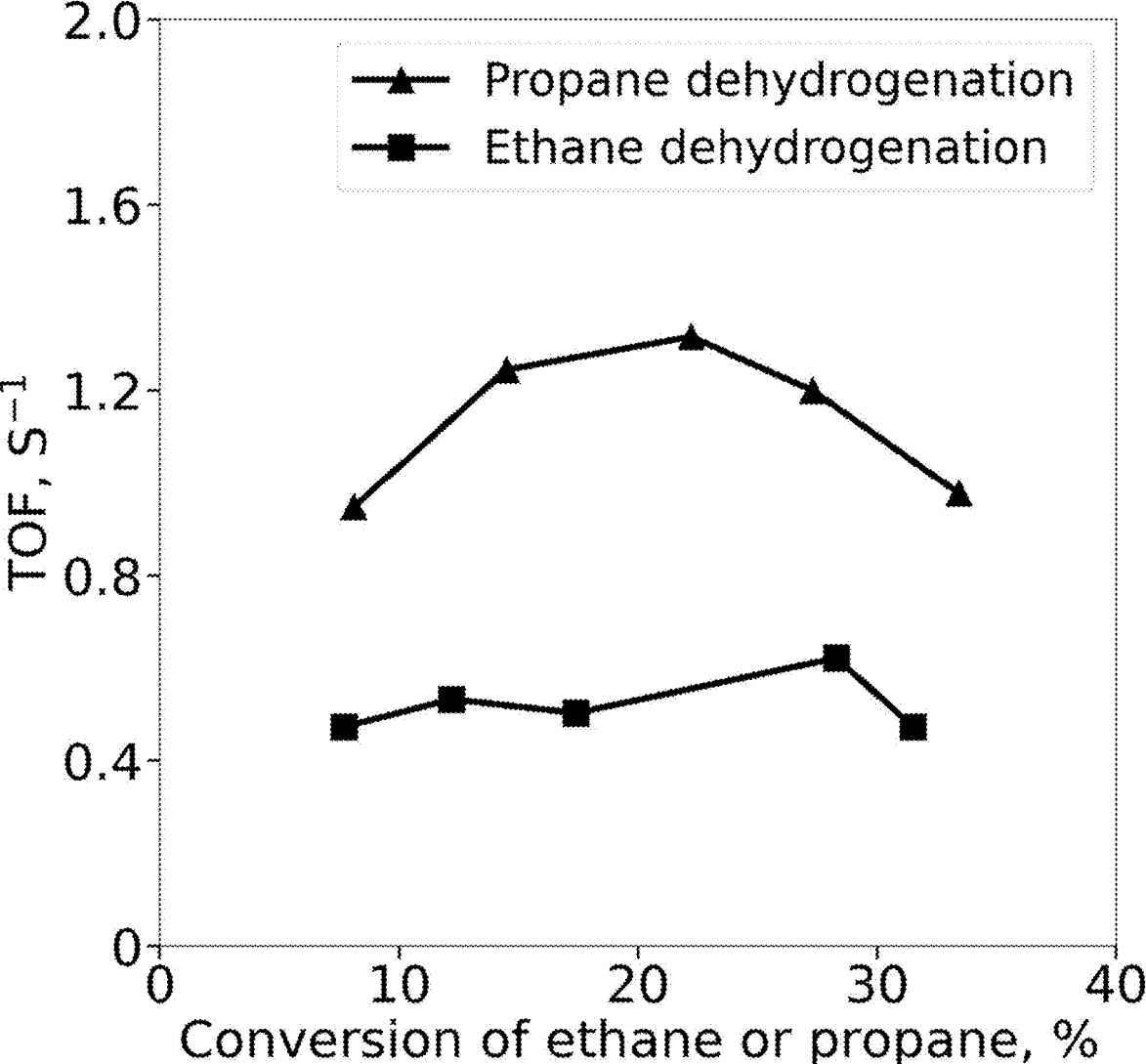
FIG. 6A-D. Electronic effects of Pt/MXene catalysts for ethane and propane dehydrogenation. (a) TOFs at various GHSV over the 0.5% Pt/MXene catalyst for ethane and propane dehydrogenation at 200 cc/min total flow rate (10% $C_3H_8$: 100 mg catalyst; 50% $C_3H_8$: 200 mg catalyst; 90% $C_3H_8$: 300 mg catalyst). (b) Surface coverage at various temperatures for Pt nanoparticle and Pt MXene catalysts. (c) Pt d density of states of Pt MXene and Pt nanoparticle catalysts. (d) A comparison of the electron density profile of the Pt nanoparticle and $Pt/Mo_2TiC_2T_x$ surface.

As compared with the $H_2$—$O_2$ titration measurement, our results show that the dispersion values measured by $H_2$ chemisorption and CO chemisorption measurements vary by only ~5% to 4%. TOFs of ethane and propane dehydrogenation were plotted in FIG. 6a. TOFs of ethane dehydrogenation fell in 0.4-0.7 $s^{-1}$, while TOFs of propane dehydrogenation were in between 0.9 to 1.2 $s^{-1}$. It suggests that although GHSVs were varied in a broad range (38-151 $h^{-1}$ for ethane, and 79-317 $h^{-1}$ for propane), the reaction rates per surface Pt atom were essentially constant for both ethane and propane. It further demonstrates surface Pt atoms were the active sites for both ethane and propane dehydrogenation.

Figure 6B:
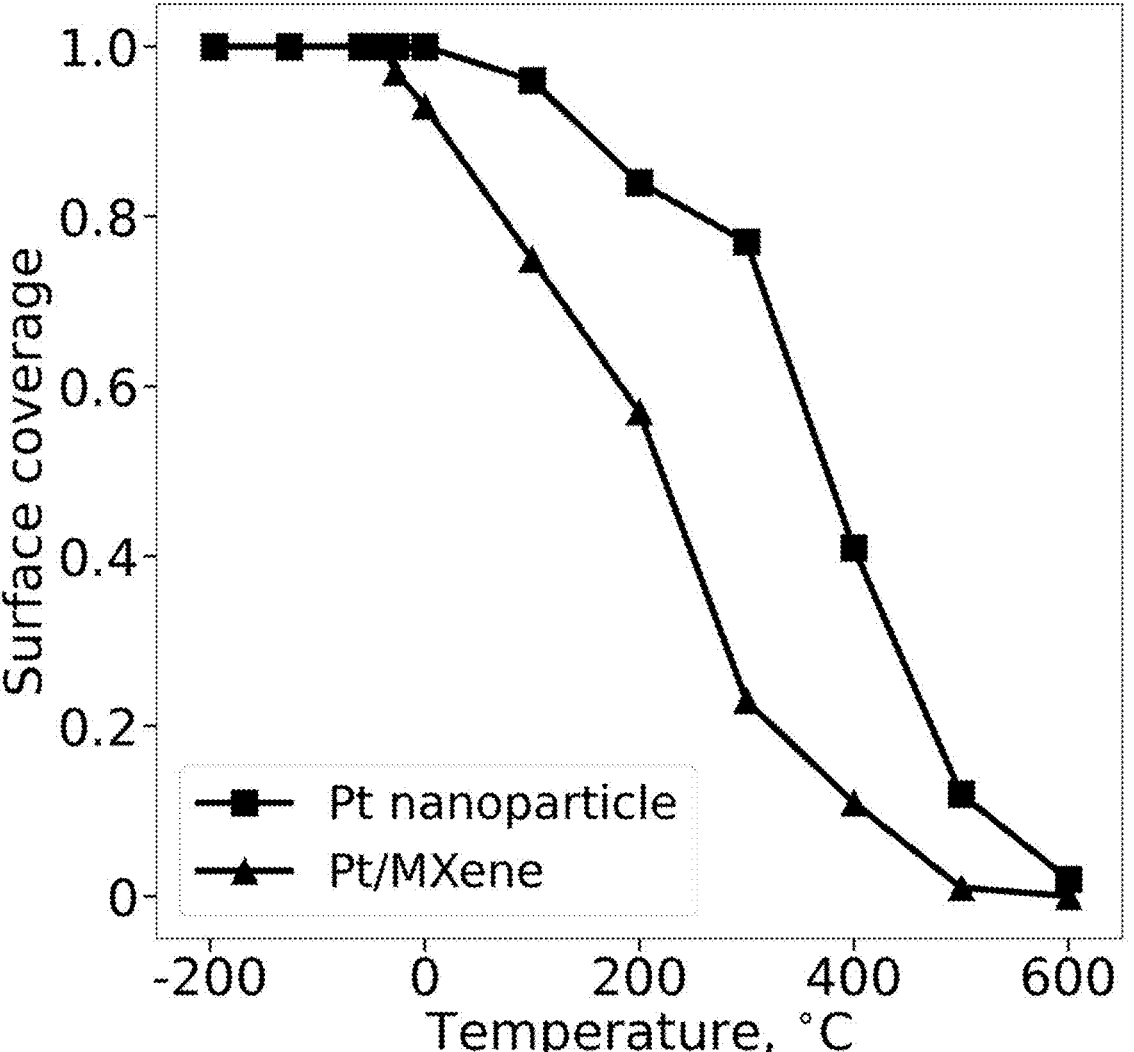
Figure 6C:
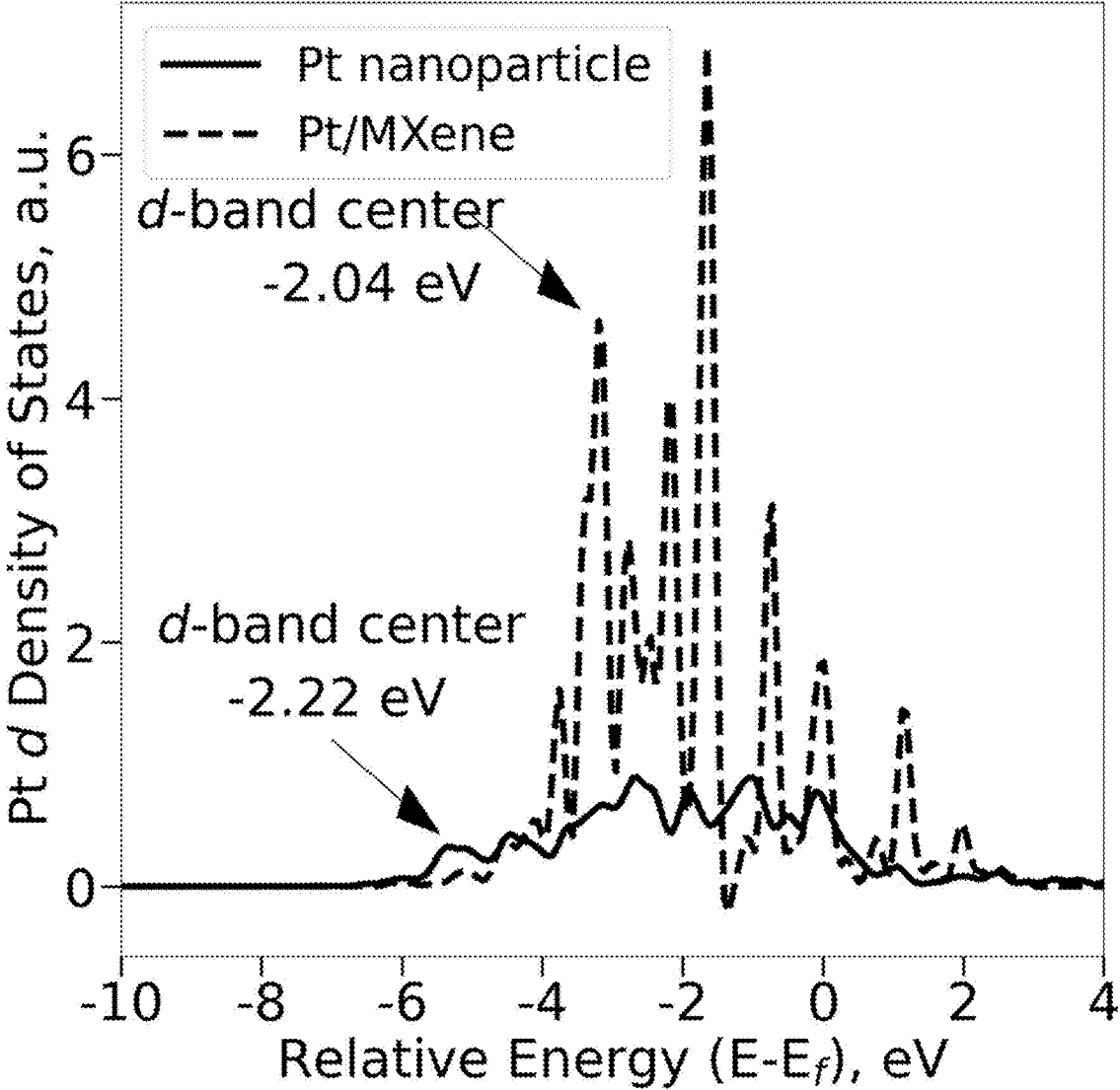

The low-temperature $H_2$ chemisorption was used to further study the coke-resistant property of the catalyst. Hydrogen surface coverage was evaluated from −196 to 600° C. for Pt nanoparticle and $Pt/Mo_2TiC_2$, respectively, as shown in FIG. 6b. The surface coverage of Pt nanoparticles exceeded that of $Pt/Mo_2TiC_2$ when the temperature was higher than 100° C., indicating weaker hydrogen adsorption over $Pt/Mo_2TiC_2$. The $Pt/Mo_2TiC_2$ catalyst exhibited high activity, i.e., 0.5-2.0 $s^{-1}$ TOF (FIG. 6c) and had a similar surface structure to that of Pt nanoparticles greater than about 2 nm, which implies that the more unoccupied 5d states of Pt nanolayer play a critical role in controlling the catalytic activity as well as the stability, which is further supported by the shifted d-band centers in density of states (DOSs) (FIG. 6c).

Figure 6D:
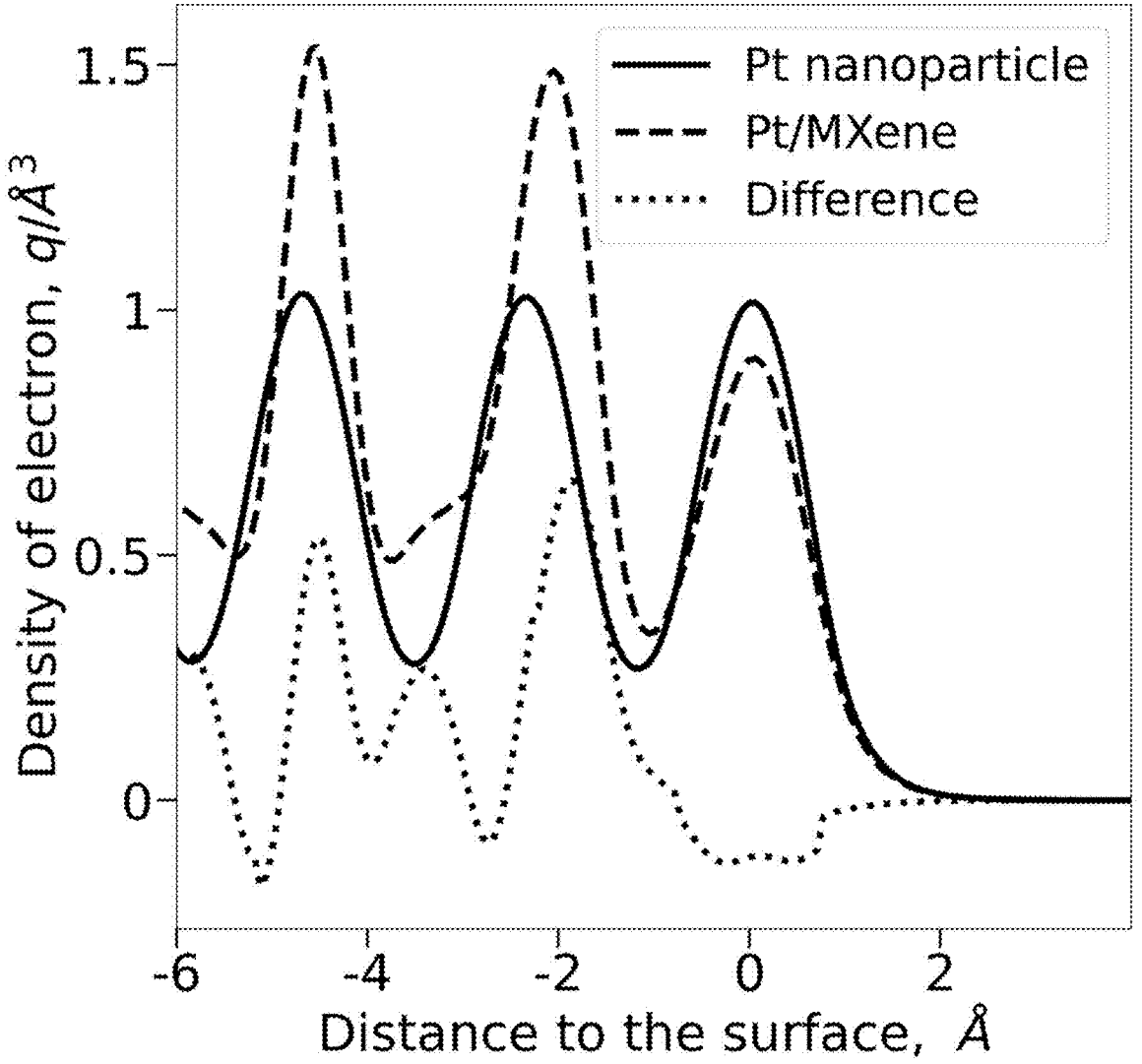

The d-band center theory claims that the binding energy of a molecule and the electronic structure of a metallic or alloy catalyst can be well associated with the d-band center energy. We calculated that the d-band center energy of the Pt nanoparticle is −2.22 eV, which is consistent with literature reports. For the Pt/MXene catalyst, the d-band center energy is calculated as −2.08 eV, which indicates electron transfer from the Pt surface layer to the MXene support, leading to a less negatively charged surface. Furthermore, the charge density difference plot propane adsorption over Pt nanoparticle and Pt/MXene catalysts also verify that the Pt/MXene surface is more positively charged, which is likely a cause of weaker adsorption. The charge density profiles (the y-axis of FIG. 6d) of Pt nanoparticle and $Pt/Mo_2TiC_2T_x$ as well as their difference are plotted in FIG. 6d with respect to the distance to the catalyst surface (the x-axis of FIG. 6d). Furthermore, the charge density differences plot between the clean surfaces and propane adsorption surfaces of both Pt nanoparticle and Pt/MXene catalysts also verifies that the Pt/MXene surface is more positively charged, which is likely a cause of weaker adsorption. The position x=0 represents the outermost Ti layer and negative values of x represents moving towards the bulk material.

There is a significant decrease in the electron density of Pt bound to $Mo_2TiC_2T_x$ compared to Pt nanoparticle. Moreover, there is a higher minimum in the electron density between Pt and $Mo_2TiC_2T_x$ than that between Pt nanoparticle and its adjacent Pt layer (near x=−1 Å), signifying more electron sharing in the former case. Taken together, these should decrease the binding between $Pt/Mo_2TiC_2T_x$ with interfacial species in comparison with the Pt nanoparticle surface.

Figure 7:
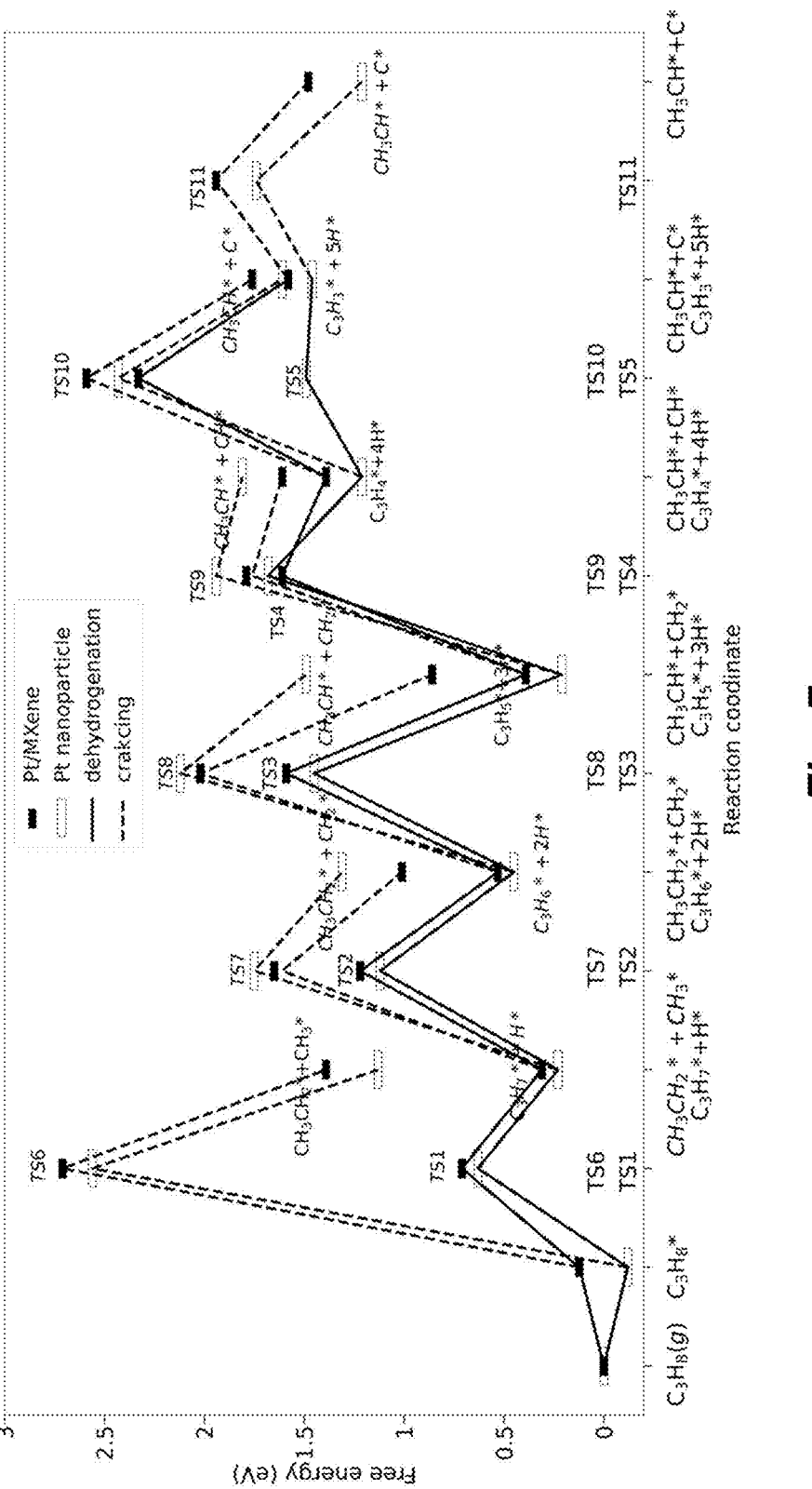
FIG. 7. DFT calculations of catalytic propane dehydrogenation and cracking over Pt/MXene and Pt(111) surfaces at 550° C.

DFT calculations were used to investigate the reaction pathways and energy changes of propane dehydrogenation to different products, including dehydrogenative and cracking products. The structures of reaction intermediates and transition states are illustrated in FIG. 7, with the free energies of the different reaction pathways. The dehydrogenation of propane involves multiple C—H activation and dissociative adsorption of alkyl species ($C_3H_7^*$, $C_3H_6^*$, $C_3H_5^*$, etc.). Our DFT calculations suggest that the scission of the first three C—H on both Pt(111) and $Pt/Mo_2TiC_2$ surfaces have similar free energies, with intermediates and transitional states on Pt(111) surface having slightly lower energies, which also agrees with the higher hydrogen coverage on Pt(111) surface than $Pt/Mo_2TiC_2$. Deep dehydrogenation ($C_3H_5^*$ to $C_3H_4^*$), however, becomes unfavorable on both surfaces as the free energy of the intermediates increases significantly (more than 0.5 eV).

On the $Pt/Mo_2TiC_2$ surface, further dehydrogenation ($C_3H_4^*$ to $C_3H_3^*$) which eventually leads to a coking product, becomes even less favorable with both increased free energy of the $C_3H_3^*$ intermediate and the larger energy barrier to overcome. In comparison, the $C_3H_4^*$ to $C_3H_3^*$ reaction on Pt(111) surface has a significantly lower energy barrier (~0.7 eV) than that of $Pt/Mo_2TiC_2$ surface, suggesting an easier path for coke formation on Pt nanoparticles. Regarding cracking reaction pathways, the free energies of the products and the transitional states are always higher than the corresponding ones of the dehydrogenation reaction, which accounts for the increased cracking products at elevated reaction temperatures.

As shown in FIG. 7, Pt(111) and $Pt/Mo_2TiC_2$ surfaces favor cracking reactions at different stages. In general, free energy differences of the cracking intermediates, dehydrogenation intermediates, and the transitional states on Pt(111) are larger by ~0.5 eV than those on $Pt/Mo_2TiC_2$ surface, which suggests that the Pt nanoparticles should have a higher selectivity (over 90%) towards dehydrogenation than cracking. However, the Pt(111) surface favors the deep dehydrogenation, therefore eventually leading to coking and the rapid deactivation of the catalyst. The significant increase of about 0.7 eV in the energy barrier in the deep dehydrogenation reaction steps explains the excellent coke-resistant property of the $Pt/Mo_2TiC_2$ catalyst.

Conclusions. Epitaxial growth of thin Pt nanolayers on the surface of $Mo_2TiC_2$ Mxene leads to strong Pt—Mo bonding at the metal-support interface, which helps anchor the Pt atoms on the MXene surface. Consequently, $Pt/Mo_2TiC_2$ catalysts exhibit stable conversion of ethane and propane to ethylene and propylene with high selectivity and excellent coke resistance. The unique Pt monolayer provides an opportunity to evaluate the electronic effect on the catalytic performance, as the surface structure of the Pt monolayers shares a similar surface structure with larger Pt nanoparticles, where the geometric effect can be minimized. Due to the altered electronic structures of the Pt nanolayers, the hydrogen adsorption on $Pt/Mo_2TiC_2$ is weaker than that on Pt nanoparticle surfaces, preventing the deep dehydrogenation which eventually leads to coking on Pt surfaces. These discoveries are important for understanding the role electronic effects play in product selectivity and catalyst stability. In addition, the metal-support interaction is dependent on the substrate and metal components, providing wide opportunities to explore high-performance MXene-supported metal catalysts, as well as reveal their structure-property relationship for broader reactions with industrial importance.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Molybdenum powder (Mo, 1-5 μm, 99%), $Pt(NH_3)_4$ $(NO_3)_2$ (99.995%), and hydrofluoric acid (48%) were purchased from Sigma-Aldrich, USA. Aluminum powder (Al, 325 mesh, 99%), titanium powder (Ti, 325 mesh, 99%), graphite powder (C, 7-11 μm, 99%), and boron nitride (BN, 97+%) were purchased from Alfa Aesar, USA. All the chemicals were used as received without further purification. The $Mo_2TiAlC_2$ powder was firstly synthesized by spark plasma sintering (SPS) of Mo/Ti/Al/C. Commercial powders of molybdenum, titanium, aluminum, and graphite were mixed in a molar ratio of 2:1:1.1:1.9. The mixture was transferred into a graphite die coated with BN. Then, the die was loaded into a Fuji-211lx SPS system and sintered at 1450° C. for 1 h under a pressure of 30 MPa. The obtained bulk $Mo_2TiAlC_2$ was then pulverized in a synthetic sapphire mortar and sieved through a 325-mesh screen. For the synthesis of $Mo_2TiC_2$ MXene, 1.0 g of the obtained $Mo_2TiAlC_2$ was slowly added to 10 mL of hydrofluoric acid (48%). The mixture was stirred for 72 h at 55° C. in a high-density polyethylene centrifugal tube. The resulting MXene was collected by centrifugation at 8900 rpm, after which the MXene was rinsed with distilled water and ethanol until the pH value reached 5-6. The $Mo_2TiC_2$ MXene powders were collected and then dried under vacuum at ambient temperature. For the synthesis of the catalyst, 0.040 g of $Pt(NH_3)_4(NO_3)_2$ was dissolved in 1 mL of deionized water (DI) to prepare a solution of 20 mg Pt per mL. Pt was loaded on $Mo_2TiC_2$ supports via incipient-wetness impregnation method. After the impregnation of Pt, the materials were dried overnight in vacuum at ambient temperature.

The X-ray absorption measurements were conducted at the Pt LIII edge (11.5640 keV) on the bending magnet beam line of the Materials Research Collaborative Access Team (MRCAT) at Sector 10 in the Advanced Photon Source, Argonne National Laboratory. The ionization chambers were optimized for the maximum current with linear response of 10% absorption in the incident ion chamber and 70% absorption in the transmission detector. A third detector in series simultaneously collected a Pt metal foil reference spectrum with each measurement for energy calibration. Solid samples were pressed into a cylindrical sample holder consisting of six wells, forming a self-supporting wafer. The sample holder was placed in a quartz reactor tube sealed with Kapton windows by two Ultra-Torr fittings through which gas could be flowed. The $Pt/Mo_2TiC_2T_x$ catalyst was heated to 550° C. in 3.5% $H_2$ for 30 min, then cooled to room temperature and flushed with He before the scan. Athena was used for energy calibration, background subtraction, and normalization of the X-ray absorption spectroscopy (XAS) data. The extended X-ray absorption fine structure (EXAFS) data were fitted by Artemis to determine the coordination number (CN), bond distance (R), energy shift ($\Delta E_o$), and Debye Waller factor ($\Delta\sigma2$). The k range for the Fourier transform of the Pt K edge was $\Delta k=3-11$ Å$^{-1}$, and the R range for the fitting was $\Delta R=1.0-3.2$ Å. The amplitude reduction factor (S2=0.80) was determined by the standard Pt foil and CN, bond distances and Debye-Waller factor were adjusted from an initial structural model until a good fit was obtained. High-angle annular dark-field scanning transmission electron microscopy (HAADF-STEM) experiments were carried out on a Titan Themis scanning transmission electron microscope equipped with a Super-X energy-dispersive X-ray spectroscopy (EDX) detector.

The low-temperature $H_2$ chemisorption uptakes were measured by loading 100 mg of the catalyst into a U-shaped quartz reactor, which was controlled at −196, −126, −59, −38, −27, and 0° C., respectively. When the catalyst was fully saturated at 0° C., the reactor was then heated to 600° C. at 10° C./min in 20 cm3/min of He. $H_2$ desorption was measured at 100, 200, 300, 400, 500, and 600° C. $H_2$ coverages at various temperatures were calculated by normalizing the corresponding $H_2$ uptakes to the saturated $H_2$ adsorption. The catalytic performance tests of propane and ethane dehydrogenation were carried out in a quartz-constructed fixed-bed reactor with I.D.=0.5 in. Prior to a test, the packed catalyst was activated in 10% $H_2$ (balanced with high purity $N_2$) at 450° C. and 100 std cc/min for 2 h. The reactor was then purged by $N_2$ at 50 std cc/min for 15 min. Different gas hourly space velocity (GHSV) values were achieved by varying the packed amount of catalysts and feed flow rates.

The standard operating conditions were 550° C., 10% $C_3H_8$ (or $C_2H_6$)+89% $N_2$+1% Ar, 200 cc/min total flow rate, and 100-200 mg catalyst. The absence of mass transfer limitations, including both internal and external diffusion, was confirmed by satisfying the Weisz and Prater criterion, while the Mears criterion was used to exclude heat transfer effects. A gas chromatography (GC) (Agilent GC6890) with both flame ionization detector (FID) and thermal conductivity detector (TCD), equipped with a Carboxen 1010 PLOT capillary column (30 m×0.53 mm) was used for quantitative analysis of products. In typical cases, following an initial transient period, the catalyst exhibited stable performance. Unless stated otherwise, all data sets were taken at 10 min TOS during the stable period. A blank test of the MXene support with no Pt loading was carried out under standard operating conditions, with the ethane and propane conversion always less than 0.03%. All experiments have carbon mass balances of 96.2%±0.5%. For the reaction experiments, good repeatability generally within less than 1.9% deviation was achieved for all quantitative analyses.

Density functional theory (DFT) calculations were performed on the MXene-Pt system using the Vienna Ab initio Simulation Package (VASP), employing the projector augmented wave method for ionic cores and the PW91 exchange-correlation functional in the generalized-gradient approximation. The plane-wave cutoff energy levels for bulk and slab calculations were set as 520 and 400 eV, respectively, while a first-order Methfessel-Paxton smearing with a width of 0.15 eV was evaluated by extrapolating to zero broadening. The energy convergence criteria for all self-consistent field calculations were set as 10-5 eV, and all structural relaxations were performed until forces were less than 0.02 eV/Å. For structural optimization of a single unit cell of the MXene monolayer, a 12×12×1 gamma centered k-point mesh was used. For larger unit cells consisting of 8×8 unit cells of the MXene monolayer and Pt film or nanoparticles, we used a 2×2×1 k-point mesh in our calculations.

A vacuum separation of more than 20 Å was kept on top of the MXene layer to prevent interaction with its periodic image. A Pt layer was inserted into two $Mo_2TiC_2T_x$ layers to represent our $Pt/Mo_2TiC_2T_x$ catalyst. The climbing-image nudged elastic band method was used to locate the structures of transition states (TSs) in the reactions. A p(4×4) Pt (111) unit cell was used for propane dehydrogenation. Each transition state was confirmed to have only one imaginary vibrational mode by vibrational normal mode analysis. All free energies were zero-point energy (ZPE)-corrected, and the change in entropies for adsorption processes was calculated by considering the temperature of the reactions in our experiments.

Example 2. Synthesis of $Pt/Mo_2TiC_2T_x$

For a typical synthesis, 0.20 g of $Pt(NH_3)_4(NO_3)_2$ (Sigma Aldrich, 99.995%) was dissolved in 1 mL of deionized water (DI) $H_2O$ to prepare 0.02 g Pt/mL. Pt was loaded on $Mo_2TiC_2T_x$ supports via incipient-wetness impregnation (IWI). The amount of Pt loading can be controlled by varying the volume of Pt solution used. After the impregnation of Pt, the materials were dried overnight under vacuum at room temperature. Fresh $Pt/Mo_2TiC_2T_x$ was directly used for kinetics tests and other treatments. For reduced $Pt/Mo_2TiC_2T_x$, the fresh $Pt/Mo_2TiC_2T_x$ powder was transferred into a tube furnace and reduced at various temperatures for at least 30 minutes under a 3% $H_2/Ar$ flow with a ramping rate of 5° C./min.

Additional methods and details of Pt/MXene preparation are described by Li et al, *Nat. Catal.* 4, 882-891 (2021), as well as U.S. Pat. No. 11,524,279 (Li et al.) filed Nov. 18, 2020, which are incorporated herein by reference.

Example 3. Method for Preparing Propylene by Propane Dehydrogenation

A gas chromatograph (GC) (Agilent GC6890) with both a flame ionization detector (FID) and a thermal conductivity detector (TCD), equipped with a Carboxen 1010 PLOT capillary column (30 m×0.53 mm), was used for quantitative analysis of products. In typical cases, following an initial transient period, the catalyst exhibited stable performance for several hours. Unless stated otherwise, all data sets were taken at 10 minutes time on stream (TOS) during the stable period. A blank test of the MXene support with no Pt loading was carried out under standard operating conditions, with the propane conversion always less than 0.03%. All experiments had carbon mass balances of 96.2±0.5%. For the reaction experiments, good repeatability generally within less than 1.9% deviation was achieved for all quantitative analyses.

The catalytic performance tests of propane dehydrogenation were carried out in a quartz-made fixed-bed reactor with I.D.=0.5 inches. Prior to a test, the packed catalyst was activated in 10% $H_2$ (balanced with high purity $N_2$) at 450° C. and 100 std cc/min for 2 hours. The reactor was then purged by $N_2$ at 50 std cc/min for 15 minutes. Different GHSV (gas hourly space velocity) values were achieved by varying the packed amount of catalyst and feed flow rates. The standard operating conditions were 550° C., 10% $C_3H_8$+90% $N_2$, 200 cc/min total flow rate, 200 mg catalyst. The absence of mass transfer limitations, including both internal and external diffusion, was confirmed by satisfying the Weisz and Prater criterion, while the Mears criterion was used to exclude heat transfer effects. One example of the dehydrogenation of propane is illustrated in the following scheme, although the specific reaction conditions can be varied.

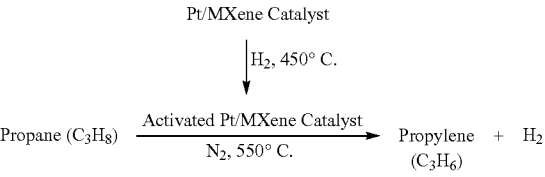

In a flow fixed-bed reactor, nonoxidative propane dehydrogenation was performed over the 0.5% $Pt/Mo_2TiC_2$ catalysts with different propane ($C_3H_8$) compositions (10%, 50%, and 90%, balanced with inert $N_2$). The catalyst exhibits different $C_3H_8$ conversion and selectivity values in the temperature range 400-600° C. Higher operating temperature leads to higher $C_3H_8$ conversion but lower $C_3H_6$ selectivity. Also, higher $C_3H_8$ concentrations result in a slightly lower conversion but relatively higher turnover frequencies (TOFs). The catalyst shows a stable trend within the 24-hour time on stream (TOS) at approximately 20% $C_3H_8$ conversion and >90% selectivity toward propylene ($C_3H_6$).

Example 4. Method for Preparing Ethylene by Ethane Dehydrogenation

Ethane dehydrogenation was carried out similar to the propane dehydrogenation described in Example 2. One example of the dehydrogenation of ethane is illustrated in the following scheme, although the specific reaction conditions can be varied.

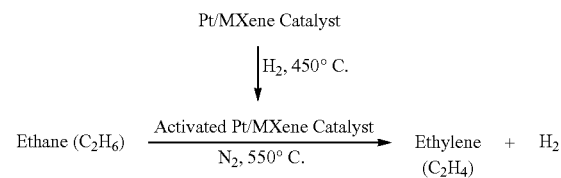

In a flow fixed-bed reactor, nonoxidative ethane dehydrogenation was performed over the 0.5% $Pt/Mo_2TiC_2$ catalysts with 10% $C_2H_6$ and 90% inert $N_2$. The catalyst exhibits different ethane ($C_2H_6$) conversion and selectivity values in the temperature range of 400-600° C. Higher operating temperatures lead to higher $C_2H_6$ conversion but lower $C_2H_4$ selectivity. The catalyst shows a stable trend within the 24-hour time on stream (TOS) at approximately 15% $C_2H_6$ conversion and >95% selectivity towards $C_2H_4$.

Example 5. DFT Computational Methods

Density functional theory (DFT) calculations were performed on the MXene-Pt system using the Vienna Ab initio Simulation Package (VASP)51, employing the projector augmented wave method for ionic cores and the PW91 form of exchange-correlation functional in the generalized-gradient approximation. The plane-wave cutoff energy levels for bulk and slab calculations were set as 520 and 400 eV, respectively, while a first-order Methfessel-Paxton smearing with a width of 0.15 eV was evaluated by extrapolating to zero broadening.

The energy convergence criteria for all self-consistent field calculations were set as $10^{-5}$ eV, and all structural relaxations were performed until forces were less than 0.02 eV/Å. For structural optimization of a single unit cell of the MXene monolayer, a 12×12×1 gamma centered k-point mesh was used. For larger unit cells consisting of 8×8 unit cells of the MXene monolayer and Pt film or nanoparticles, a 2×2×1 k-point mesh was used in the calculations. A vacuum separation of more than 20 Å was kept on top of the MXene layer to prevent interaction with its periodic image.

A Pt layer was inserted into two $Mo_2TiC_2T_x$ layers to represent the $Pt/Mo_2TiC_2T_x$ catalyst. The climbing-image nudged elastic band method was used to locate the structures of transition states (TS) in the reactions (FIG. 7). A p(4×4) Pt (111) unit cell was used for propane dehydrogenation. Each transition state was confirmed to have only one imaginary vibrational mode by vibrational normal mode analysis. All free energies were ZPE-corrected, and the change in entropies for adsorption processes was calculated using the operating reaction temperature.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for dehydrogenating a hydrocarbon comprising:
   a) activating a catalyst with a hydrogen source to provide an activated catalyst, wherein the catalyst comprises:
      i) a MXene support of Formula II:

$$Mo_2TiC_2T_x \qquad (II);$$

wherein Mo is an early transition metal; and $T_x$ is a surface functional group wherein x is 0-10;
      ii) a noble metal, wherein atoms of the noble metal occupy crystal lattice nodes at the basal plane of the MXene support, the atoms of the noble metal are supported by a metallic bond to the early transition metal, the noble metal has one to five nanostructured layers of its atoms on the MXene support, and loading of the noble metal on the MXene support is less than 5% w/w based on the weight of the catalyst; and
   b) contacting the activated catalyst and a hydrocarbon at a temperature of at least about 350° C., optionally in the presence of an inert gas, for a period of time sufficient to dehydrogenate the hydrocarbon;
      thereby providing a non-oxidatively dehydrogenated hydrocarbon.

2. The method of claim 1 wherein the noble metal is platinum, iridium, rhodium, palladium, ruthenium, or a combination thereof.

3. The method of claim 1 wherein the surface functional group is halo, hydroxyl, oxo, or a combination thereof.

4. The method of claim 1 wherein the catalyst is a $Mo_2TiC_2T_x$ support loaded with platinum, wherein the platinum loading is 0.2 wt. % to 0.4 wt. %.

5. The method of claim 1 wherein the loading of the noble metal on the MXene support is about 0.1 weight percent to about 4.5 weight percent, with respect to the weight of the MXene support.

6. The method of claim 1 wherein the catalyst is a $Mo_2TiC_2T_x$ support loaded with platinum, wherein the platinum loading about 0.1 wt. % to about 2 wt. %.

7. The method of claim 1 wherein the hydrocarbon is propane or ethane.

8. The method of claim 1 wherein activating the catalyst comprises heating the catalyst and the hydrogen source at temperature above 250° C., wherein the hydrogen source is optionally a 20-40% v/v mixture of hydrogen gas in an inert gas.

9. The method of claim 1 wherein contacting the activated catalyst and the hydrocarbon is carried out in the presence of an inert gas, thereby forming a gas mixture comprising the hydrocarbon and the inert gas, wherein the gas mixture comprises about 5% v/v to about 95% v/v hydrocarbon.

10. The method of claim 9 wherein the gas mixture comprises about 5% v/v to about 15% v/v hydrocarbon.

11. The method of claim 9 wherein the activated catalyst and the gas mixture are heated at a temperature of about 350° C. to about 700° C.

12. The method of claim 9 wherein the activated catalyst and the gas mixture are heated at a temperature of about 500° C. to about 650° C.

13. The method of claim 9 wherein the contacting in step b) is at a gas space velocity of about 100 cc/min to about 300 cc/min.

14. The method of claim 9 wherein the contacting in step b) is carried out at a total flow rate of about 50 cc/min to about 150 cc/min per 100 mg of catalyst.

15. A method for dehydrogenating propane comprising:
   a) activating a catalyst by heating the catalyst in the presence of hydrogen gas to provide an activated catalyst, wherein the catalyst comprises:
      i) a MXene support represented by Formula (II):

$$MO_2TiC_2T_x \qquad (II);$$

wherein $T_x$ is a surface functional group wherein x is 0-10; and
      ii) platinum metal, wherein atoms of the platinum metal occupy crystal lattice nodes at the basal plane of the MXene support, the atoms of the platinum metal are supported by a metallic bond to molybdenum atom of the MXene support, the platinum metal has one to five nanostructured layers of its atoms on the MXene support, and loading of the platinum metal on the MXene support is less than 5% w/w based on the weight of the catalyst; and
   b) contacting the activated catalyst and a mixture comprising propane and nitrogen gas at a temperature of at least about 350° C., for a period of time sufficient to dehydrogenate the propane;
      wherein the contacting is at a gas space velocity of about 50 cc/min to about 150 cc/min per 100 mg of catalyst, thereby non-oxidatively dehydrogenating propane to provide propylene.

16. The method of claim 15 wherein the mixture comprising propane and nitrogen gas comprises about 5% v/v to about 25% v/v propane, or about 5% v/v to about 15% v/v propane.

17. The method of claim 15 wherein the activated catalyst, and the mixture comprising propane and nitrogen gas, are heated at a temperature of about 500° C. to about 600° C.

18. A method for dehydrogenating ethane comprising:
   a) activating a catalyst by heating the catalyst in the presence of hydrogen gas to provide an activated catalyst, wherein the catalyst comprises:
      i) a MXene support represented by Formula (II):

$$MO_2TiC_2T_x \qquad (II);$$

wherein $T_x$ is a surface functional group wherein x is 0-10; and
      ii) platinum metal, wherein atoms of the platinum metal occupy crystal lattice nodes at the basal plane of the MXene support, the atoms of the platinum metal are supported by a metallic bond to molybdenum atom of the MXene support, the platinum metal has one to five nanostructured layers of its atoms on the MXene support, and loading of the platinum metal on the MXene support is less than 5% w/w based on the weight of the catalyst; and
   b) contacting the activated catalyst and a mixture comprising ethane and nitrogen gas at a temperature of at least about 350° C., for a period of time sufficient to dehydrogenate the ethane;

wherein the contacting is at a gas space velocity of about 50 cc/min to about 150 cc/min per 100 mg of catalyst, thereby non-oxidatively dehydrogenating ethane to provide ethylene.

19. The method of claim 18 wherein the mixture comprising ethane and nitrogen gas comprises about 10% v/v to about 90% v/v ethane, or about 5% v/v to about 15% v/v of ethane.

20. The method of claim 18 wherein the activated catalyst and the mixture comprising ethane and nitrogen gas are heated at a temperature of about 550° C. to about 650° C.

\* \* \* \* \*